United States Patent [19]

Ryu et al.

[11] Patent Number: 5,631,208
[45] Date of Patent: May 20, 1997

[54] HERBICIDAL CYCLOHEXANE-1,3-DIONE DERIVATIVES AND THEIR PREPARATION PROCESS

[75] Inventors: Eung K. Ryu; Kyoung M. Kim; Hyoung R. Kim, all of Daejeon; Jong H. Song, Chungchongbuk-do; Jae N. Kim; Jin S. Kim, both of Daejeon, all of Rep. of Korea

[73] Assignee: Korea Research Institute of Chemical Technology, Rep. of Korea

[21] Appl. No.: 379,432

[22] PCT Filed: Aug. 6, 1993

[86] PCT No.: PCT/KR93/00069

§ 371 Date: Apr. 24, 1995

§ 102(e) Date: Apr. 24, 1995

[87] PCT Pub. No.: WO94/03443

PCT Pub. Date: Feb. 17, 1994

[30] Foreign Application Priority Data

Aug. 7, 1992 [KR] Rep. of Korea ............ 92-14193

[51] Int. Cl.⁶ .......................... A01N 43/12; A01N 35/10; C07L 307/78
[52] U.S. Cl. .......................... 504/176; 504/298; 549/467; 549/469
[58] Field of Search .................... 549/469, 467; 504/298, 176

[56] References Cited

U.S. PATENT DOCUMENTS

| | | | |
|---|---|---|---|
| 3,821,256 | 6/1974 | Vollrath et al. | 260/346.2 |
| 3,950,420 | 4/1976 | Sawaki et al. | 260/563 C |
| 4,298,615 | 11/1981 | Schwarz et al. | 424/285 |
| 4,426,385 | 1/1984 | Cain | 424/263 |
| 4,511,391 | 4/1985 | Serban et al. | 71/88 |
| 4,639,267 | 1/1987 | Farquharson et al. | 71/98 |
| 4,652,303 | 3/1987 | Watson et al. | 71/88 |
| 4,668,275 | 5/1987 | Keil et al. | 71/88 |
| 4,734,121 | 3/1988 | Keil et al. | 71/88 |
| 5,149,834 | 9/1992 | Matumoto et al. | 540/292 |

FOREIGN PATENT DOCUMENTS

| | | |
|---|---|---|
| 464655 | 9/1975 | Australia . |
| 2049077 | 3/1992 | Canada . |
| 2822304 | 11/1975 | Germany . |
| 1461170 | 1/1977 | United Kingdom . |

OTHER PUBLICATIONS

Chemical Abstracts, vol. 89, No. 3, issued 1978, Jul. 17 (Columbus, Ohio, U.S.A.), Mazurczak, Jerzy et al. "2,4 Diaminopyrimidine derivatives", p. 656, column 2, the abstract no. 24 352e.

Chemical Abstracts, vol. 98, No. 19, issued 1983, May 09 (Columbus, Ohio, U.S.A.), Kovtunenko, V.A. et al., "Analogs of 2,5-dimethoxy-4-methylphenylisopropylamine. 1-(5 Methoxy-2-methyl-2,3- dihydrobenzofuran-6-yl)-2-=aminopropane.", p. 497, column 2, the abstract No. 160 538h.

*Primary Examiner*—C. Warren Ivy
*Assistant Examiner*—Raymond Covington
*Attorney, Agent, or Firm*—Finnegan, Henderson, Farabow, Garrett & Dunner, L.L.P.

[57] ABSTRACT

The present invention relates to novel cyclohexane-1,3-dione derivatives of formula (I) useful as herbicides and plant-growth regulants.

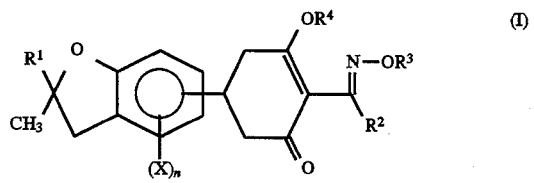

wherein,

X is selected from the group consisting of hydrogen, $C_1$–$C_6$ alkyl, $C_2$–$C_6$ alkoxy, halogen, $C_1$–$C_6$ haloalkyl, nitro, cyano, $C_1$–$C_6$ alkylthio, $C_1$–$C_6$ alkylsulfinyl, $C_1$–$C_6$ alkylsulfonyl, sulfamoyl, N-($C_1$–$C_6$ alkyl) sulfamoyl and N,N-di($C_1$–$C_6$ alkyl) sulfamoyl group;

(X)n represents number of X substituents which may be the same or different on benzene ring, where n is 1, 2 or 3.

Also, cyclohexyl moiety, one of the substituents on benzofuran ring, is substituted at 4, 5, 6 or 7 position. The (X)n can't be filled only with hydrogens and the (X)n can substitute position where cyclohexyl moiety is not substituted;

$R^1$ is selected from hydrogen and $C_1$–$C_4$ alkyl group;

$R^2$ is selected from $C_1$–$C_6$ alkyl, $C_2$–$C_6$ alkenyl and $C_2$–$C_6$ alkynyl group;

$R^3$ is selected from hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkoxyalkyl, $C_2$–$C_6$ alkylthioalkyl, benzyl and $C_2$–$C_6$ haloalkanoyl group;

$R^4$ is selected from hydrogen, alkali metal cation, alkaline earth metal cation, $C_1$–$C_4$ alkanoyl, $C_1$–$C_4$ haloalkanoyl and benzoyl group.

18 Claims, No Drawings

HERBICIDAL CYCLOHEXANE-1,3-DIONE DERIVATIVES AND THEIR PREPARATION PROCESS

This application is a 371 of PCT/KR93/00069 filed Aug. 6, 1993.

BACKGROUND OF THE INVENTION

1. Technical Field

The present invention relates to novel cyclohexane-1,3-dione derivatives of the following formula (I) useful as herbicides and plant-growth regulants.

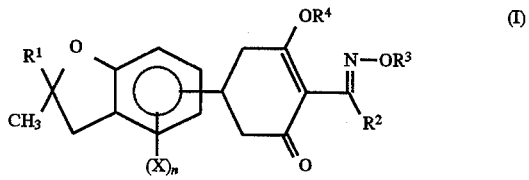

wherein,

- X is selected from the group consisting of hydrogen, $C_1-C_6$ alkyl, $C_2-C_6$ alkoxy, halogen, $C_1-C_6$ haloalkyl, nitro, cyano, $C_1-C_6$ alkylthio, $C_1-C_6$ alkylsulfinyl, $C_1-C_6$ alkylsulfonyl, sulfamoyl, N-($C_1-C_6$ alkyl) sulfamoyl and N,N-di($C_1-C_6$ alkyl) sulfamoyl group;
- (X)n represents number of X substituents which may be the same or different on benzene ring, where n is 1, 2 or 3.

Also, cyclohexyl moiety, one of the substituents on benzofuran ring, is substituted at 4, 5, 6 or 7 position. The (X)n can't be filled only with hydrogens and the (X)n can substitute position where cyclohexyl moiety is not substituted;

- $R^1$ is selected from hydrogen and $C_1-C_4$ alkyl group;
- $R^2$ is selected from $C_1-C_6$ alkyl, $C_2-C_6$ alkenyl and $C_2-C_6$ alkynyl group;
- $R^3$ is selected from hydrogen, $C_1-C_6$ alkyl, $C_1-C_6$ haloalkyl, $C_2-C_6$ alkenyl, $C_2-C_6$ haloalkenyl, $C_2-C_6$ alkoxyalkyl, $C_2-C_6$ alkylthioalkyl, benzyl and $C_2-C_6$ haloalkanoyl group;
- $R^4$ is selected from hydrogen, alkali metal cation, alkaline earth metal cation, $C_1-C_4$ alkanoyl, $C_1-C_4$ haloalkanoyl and benzoyl group.

2. Description of the Related Art

Cyclohexane-1,3-dione derivatives and their herbicidal activity were already known in the art. For example, Alloxidim-sodium (Australian Patent No. 464,655; United Kingdom Patent No. 1,461,170; U.S. Pat. No. 3,950,420) and Sethoxydim (Germany Patent No. 2,822,304) have come into the market as grass herbicides. Cyclohexane-1,3-dione derivatives having phenyl substituent (U.S. Pat. No. 4,511,391, U.S. Pat. No. 4,639,267 and U.S. Pat. No. 4,652,303) which have similar structure to our invention has been known. This present invention differs from the compounds having 2,3-dihydrobenzofurans disclosed in U.S. Pat. No. 4,511,391, in which 2-position of benzofurans were claimed only as methylene group.

In addition, the benzofuran moieties in the present invention can not be synthesized by the methods of the synthesis of the benzofurans disclosed in U.S. Pat. No. 4,511,391. The compounds in the present invention showed good rice tolerance, while the compound in the U.S. Pat. No. 4,511,391 showed not.

Furthermore a part of compounds developed by these inventors similar to the above formula (I) but differ in substituent of (X)n on benzene ring.

Therefore, with consideration as to the aforesaid points the present inventors have made efforts to develop new herbicidal compounds which have powerful herbicidal activity and good selectivity, especially useful for selective control barnyardgrass species in upland and paddy rice.

SUMMARY OF THE INVENTION

The object of the present invention is provide novel compounds of formular (I) and its preparation processes with strong herbicidal activities, useful as selective herbicides, especially for Gramineae grasses.

Another object is to provide herbicidal composition containing a compound of formula (I) as active ingredient.

DETAILED DESCRIPTION OF THE INVENTION

The present invention is identified as cyclohexane-1,3-dione derivatives of the following formula (I), and agricultural preparations containing compounds of the formula (I) as an active ingredient.

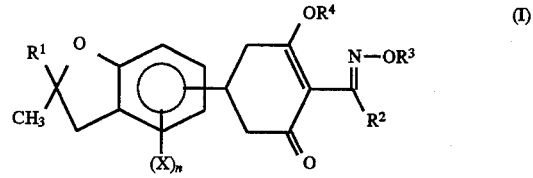

wherein, X, (X)n, $R^1$, $R^2$, $R^3$ and $R^4$ are respectively defined as described above.

In the formula (I) according to the present invention the preferred compounds are as follows: X is selected from the group consisting of hydrogen, halogen and $C_1-C_6$ alkyl group, (X)n represents number of X substituents on benzene ring where n is 1, 2 or 3; $R^1$ is selected from the group consisting of hydrogen and $C_1-C_6$ alkyl group; $R^2$ is selected from the group consisting of $C_1-C_6$ alkyl group; $R^3$ is selected from the group consisting of hydrogen, $C_1-C_6$ alkyl, $C_2-C_6$ alkenyl and $C_2-C_6$ haloalkenyl; $R^4$ is hydrogen.

Among above compounds, more preferred derivatives are as follows: $R^1$ is selected from the group consisting of $C_1-C_6$ alkyl group; $R^3$ is selected from the group consisting of $C_1-C_6$ alkyl, $C_2-C_6$ alkenyl and $C_2-C_6$ haloalkenyl group; $R^4$ is hydrogen. Among above the derivatives the most preferred derivatives are as follows: X is methyl and n is 3; $R^1$ is selected from the group consisting of methyl and ethyl; $R^2$ is selected from the group consisting of ethyl and propyl; $R^3$ is selected from the group consisting of methyl, ethyl, allyl, crotyl, 2-chloroallyl and 3-chloroallyl.

Among the compounds of the present invention, the compounds of the following formula (I-a), (I-b), (I-c), (I-d) are especially preferred.

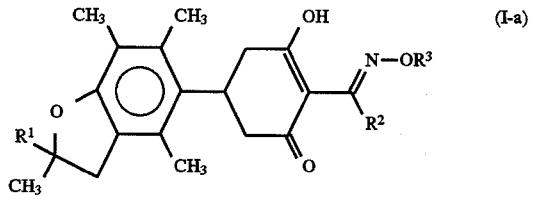

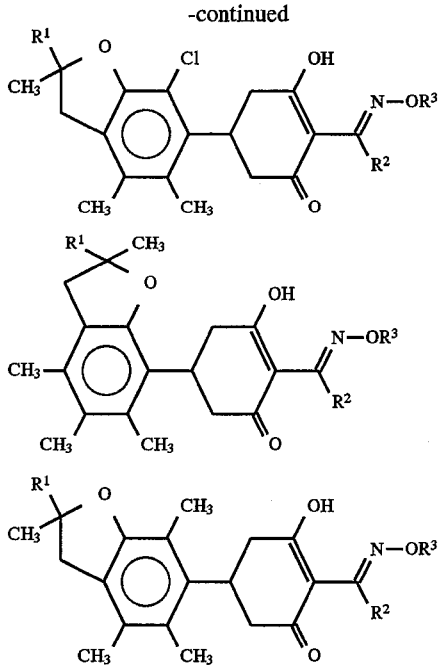

Typical compounds of the above formula (I) according to the present invention are as follows:

5-(2,3-dihydro-2,2,4,6,7-pentamethylbenzofuran-5-yl)-2-[1-(ethoxyimino)propyl]-3-hydroxycyclohex-2-en-1-one 5-(2,3-dihydro-2,2,4,6,7-pentamethylbenzofuran-5-yl)-2-[1-(ethoxyimino)butyl]-3-hydroxycyclohex-2-en-1-one 2-[1-(allyloxyimino)butyl]-5-(2,3-dihydro-2,2,4,6,7-pentamethylbenzofuran-5-yl)-3-hydroxycyclohex-2-en-1-one 5-(7-chloro-2,3-dihydro-2,2,4,5-tetramethylbenzofuran-6-yl)-2-[1-(ethoxyimino)propyl]-3-hydroxycyclohex-2-en-1-one 5-(2,3-dihydro-2,2,4,5,6-pentamethylbenzofuran-7-yl)-2-[1-(ethoxyimino)propyl]-3-hydroxycyclohex-2-en-1-one 5-(2,3-dihydro-2,2,4,5,7-pentamethylbenzofuran-6-yl)-2-[1-(ethoxyimino)propyl]-3-hydroxycyclohex-2-en-1-one If should be recognized that when $R^4$ is hydrogen the compounds of the present invention may exist in any one of four tautomeric forms as shown below.

wherein, $(X)n$, $R^1$, $R^2$ and $R^3$ are respectively defined as described above.

The formula (I) of the present invention are useful as herbicides of pre-emergence and post-emergence treatment, especially selective herbicides against monocotyledonous plants.

Especially the compounds of the present invention are safe for rice (ORYSA) and wheat (TRZAW), which are Gramineae plants, and have strong herbicidal activity against barnyardgrass (ECHOR) and wildoat (*Avena fatua* L., AVEFA), therefore the compounds of the present invention are very useful as herbicides when rice (ORYSA) and wheat (TRZAW) are cultivated.

The herbicidal composition containing the compound of the present invention as effective ingredient is formulated according to an usual method, and has selectively herbicidal effects against wild grasses in crops of cultivated plants at some rates of application.

According to the present invention, preparation processes of compound (I) and their intermediates are shown in Scheme A.

In the following reaction Scheme A, cyclohexane-1,3-dione derivatives of the following formula (II) is prepared in the presence of acid chloride or acid anhydride such as $C_2$–$C_7$ alkanoic acid, $C_3$–$C_7$ alkenoic acid or $C_3$–$C_7$ alkynoic acid in an inert organic solvent to obtain the cyclohenxenone ester derivatives of the following formula (III). 2-Acyl-1,3-cyclohexanedione derivatives of the following formula (IV) is obtained by rearrangement of compound (III) in the presence of catalyst in an inert organic solvent.

The resulted compound (IV) is reacted with 1:1 molar ratio of O-substituted-hydroxylamine hydrochloride ($NH_2OR^3$•HCl) and base catalyst in an alcohol solvent to obtain the compound of the following formula (I), $R^4$=H.

Acetate, carbonate and hydroxide of alkali metal or alkaline earth metal are used as a base.

To obtain the compound of the following formula (I) ($R^4 \neq H$), the compound (I) ($R^4$=H) is reacted with hydroxide of alkali metal or alkaline earth metal, acyl halide, haloacyl halide or benzoyl halide.

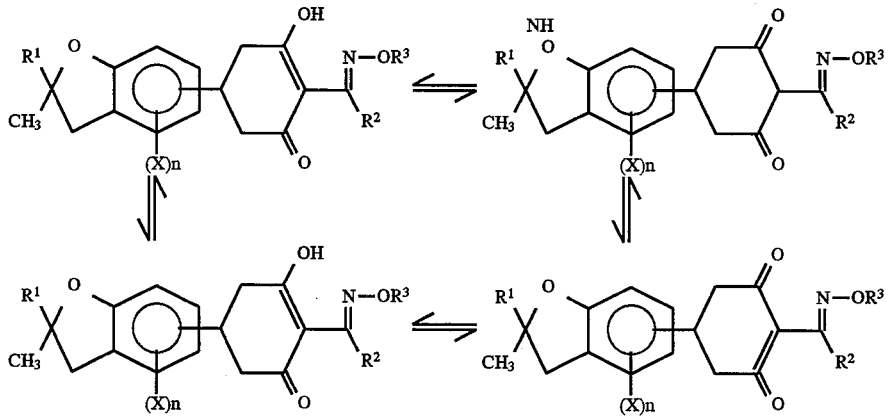

[Scheme A]

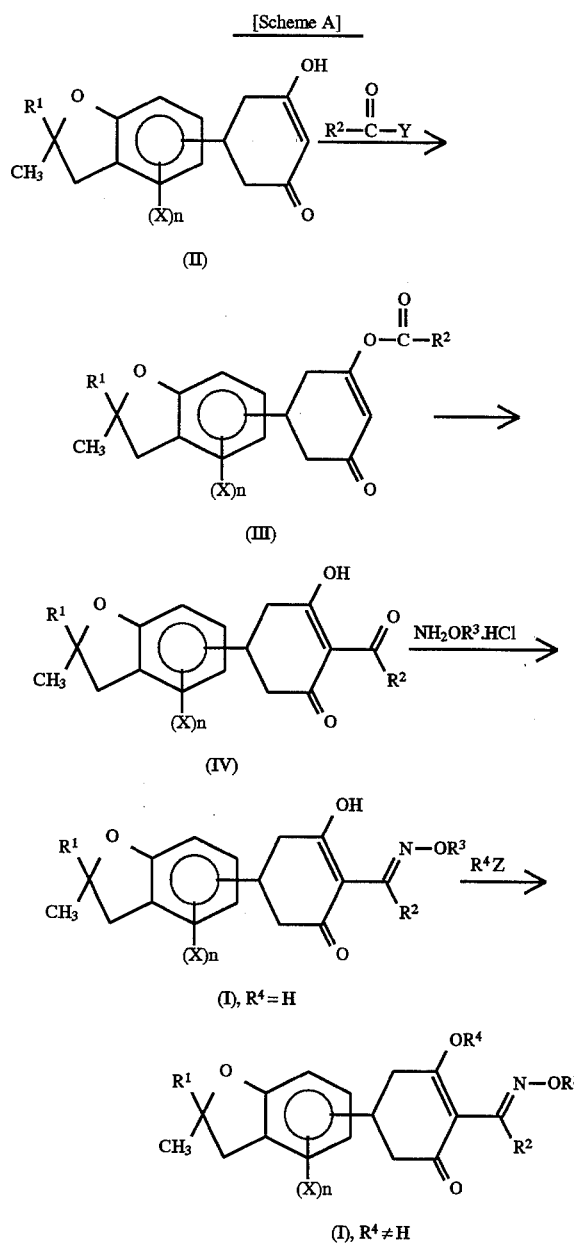

wherein, $R^2$, $R^2$, $R^3$, $R^4$ and $(X)n$ are respectively defined as described above;

Y is halogen or —O—CO—$R^2$ group;

Z is halogen or hydroxide.

In Scheme A, for the rearrangement of cyclohexenone ester of the above formula (III), pyridine, 4-aminopyridine, 4-(dimethylamino) pyridine or 1,8-diazabicyclo[5.4.0] undec-7-ene are used as catalysts and nonpolar solvent such as benzene, toluene, xylene, etc. are used as solvents.

The compound of formula (II) and the compound of formula (IV) are novel compounds and the preparation processes of novel compound (II) are as follows:

In Scheme B, benzalacetone of the following formula (V) is reacted with malonic ester in the presence of alkali metal methoxide at the boiling, temperature of methanol to obtain cyclohexane-1,3-dione-4-carboxylic acid of the following formula (VI). And the compound of above formula (II) can be prepared by the decarboxylation of compound (VI).

[Scheme B]

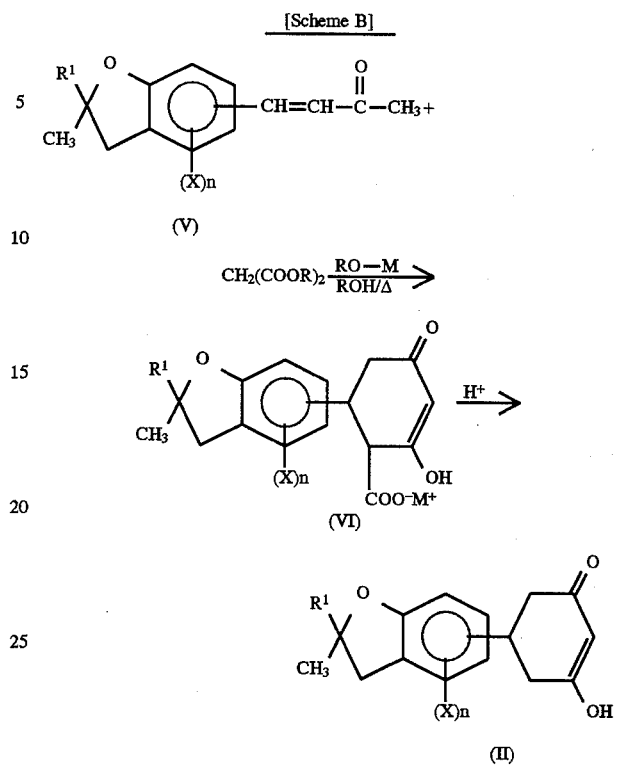

wherein, $R^1$, $R^2$, $R^3$ and $(X)n$ are respectively defined as described above;

R is $C_1$–$C_4$ alkyl group;

M is alkali metal or alkaline earth metal.

In Scheme B, the reaction of benzalacetone of the above formula (V) and malonic ester is proceeded in the presence of alkali metal or alkaline earth metal alkoxide in absolute alcohol, and decarboxylation is proceeded in the presence of strong acid such as hydrochloric acid or sulfuric acid.

Benzalacetone of the above formula (V) in Scheme B is prepared by condensation of arylaldehyde of the following formula (VII) and acetone in the presence of base catalyst such as alkali metal or alkali earth metal hydroxide in a mixture of water and alcohol.

[Scheme C]

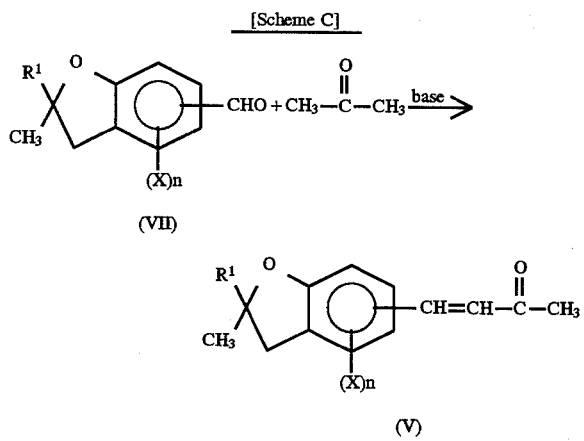

In Scheme C, 2,3-dihydrobenzofuran aldehyde derivatives of the above formula (VII), which are novel compounds and intermediates of the present invention, are prepared by the following reaction Scheme D.

[Scheme D]

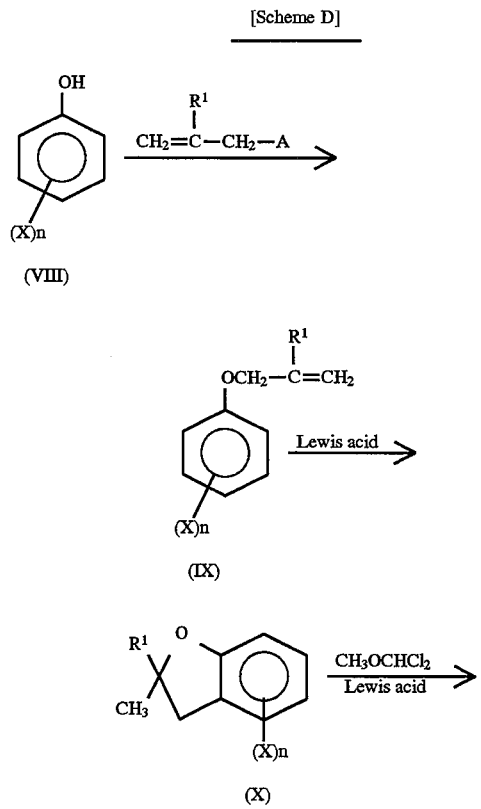

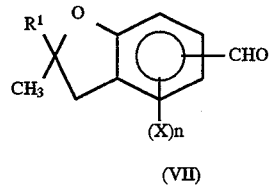

wherein,
(X)n and $R^1$ are respectively defined as described above; A is halogen.

Phenol of the following formula (VIII) is reacted with substituted allyl halide in the presence of base to obtain allyl phenyl ether of the following formula (IX), which is converted by Claisen rearrangement into 2,3-dihydrobenzofuran of the following formula (X) in the presence of Lewis acid.

The compound of formula (X) is reacted with α,α-dichloromethyl methyl ether in the presense of Lewis acid to afford the compound of formula (VII).

The method of introducing aldehyde group into the compound of formula (X) was disclosed in Organic Synthesis, Coll. Vol. 49 and U.S. Pat. No. 4,511,391.

The above reaction is carried out in an inert solvent such as acetone, N,N-dimethylformamide, dimethyl sulfoxide alcohols or polyhaloalkane, etc. with Lewis acid such as $AlCl_3$, $FeCl_3$, $TiCl_4$, $SnCl_4$ or $BF_3 \cdot OEt_2$, etc.

Base catalysts in Scheme D are metal bases such as carbonate, bicarbonate, acetate, alkoxide or hydroxide containing alkali metal or alkaline earth metal or organic bases such as pyridine or triethylamine.

Aforesaid preparation processes constitute the major object of the present invention.

Novel compounds of above formula (I), which are divided into formula (I-a), (I-b), (I-c) and (I-d), are typically listed in following Table 1–4 respectively.

TABLE 1

(I-a)

| Compound No. | $R^2$ | $R^3$ | m.p. (°C.) | $^1$H NMR ($CDCl_3$, δ in ppm) |
|---|---|---|---|---|
| 1 | $C_2H_5-$ | $C_2H_5-$ | | 1.0–1.5(2t, 6H), 1.5(s, 6H), 2.1(s, 3H), 2.2–2.3(2s, 6H), 2.5–2.8(m, 2H), 2.8–3.3(m, 6H), 3.7–3.9(m, 1H), 4.0–4.3(q, 2H), 14.1(br, 1H) |
| 2 | " | $n$-$C_3H_7-$ | 108 | 1.0–1.3(2t, 6H), 1.5(s, 6H), 1.7(m, 2H), 2.1(s, 3H), 2.2–2.3(2s, 6H), 2.5–2.7(m, 2H), 2.5–2.7(m, 2H), 2.8–3.2(m, 6H), 3.6–3.9(m, 1H), 4.0–4.2(t, 2H), 14.3(br, 1H) |
| 3 | " | $CH_2=CH-CH_2-$ | 91–92 | 1.1(t, 3H), 1.45(s, 6H), 2.1(s, 3H), 2.2–2.3(2s, 6H), 2.4–2.7(m, 2H), 2.8–3.2(m, 6H), 3.6–4.0(m, 1H), 4.5–4.6(d, 2H), 5.2–5.5(m, 2H), 5.7–6.0(m, 1H), 14.5(br, 1H) |
| 4 | " | $ClCH=CH-CH_2-$ | 104–106 | 1.1(t, 3H), 1.45(s, 6H), 2.1(s, 3H), 2.3(s, 6H), 2.5–2.7(m, 2H), 2.8–3.2(m, 6H), 3.8–4.0(m, 1H), 4.6–4.9(2d, 2H), 5.9–6.5(m, 2H), 13.9(br, 1H) |

TABLE 1-continued

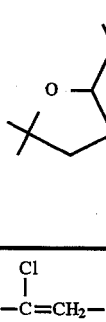

(I-a)

| Compound No. | R² | R³ | m.p. (°C.) | ¹H NMR (CDCl₃, δ in ppm) |
|---|---|---|---|---|
| 5 | " | CH₂—C(Cl)=CH₂— | 110–112 | 1.2(t, 3H), 1.4(s, 6H), 2.1(s, 3H), 2.4(s, 6H), 2.5~2.7(m, 2H), 2.8~3.1(m, 6H), 3.8~4.0(m, 1H), 4.7(s, 2H), 5.5~5.7(2d, 2H), 14.1(br, 1H) |
| 6 | " | 2-Cl-C₆H₄-CH₂— | | 1.2(t, 3H), 1.4(s, 6H), 2.1(s, 6H), 2.3(s, 6H), 2.4~2.7(m, 2H), 2.8~3.3(m, 6H), 3.4~3.9(m, 1H), 5.2(s, 2H), 7.3~7.5(m, 4H), 13.5(br, 1H) |
| 7 | " | 4-Cl-C₆H₄-CH₂— | 124–126 | 1.2(t, 3H), 1.4(s, 6H), 2.1(s, 3H), 2.3(s, 6H), 2.4~2.7(m, 2H), 2.8~3.4(m, 6H), 3.7~3.9(m, 1H), 5.3(s, 2H), 7.3~7.5(d, 4H), 13.5(br, 1H) |
| 8 | C₂H₅— | 2,4-Cl₂-C₆H₃-CH₂— | | 1.2(t, 3H), 1.4(s, 6H), 2.0(s, 3H), 2.3(s, 6H), 2.4~2.7(m, 2H), 2.8~3.1(m, 6H), 3.8~4.0(m, 1H), 5.2(s, 2H), 13.2(br, 1H) |
| 9 | n-C₃H₇— | C₂H₅— | 114–115 | 1.0(t, 3H), 1.25(t, 3H), 1.4(s, 6H), 1.5(t, 2H), 2.0(s, 3H), 2.3(s, 6H), 2.5~3.1(m, 8H), 3.5~3.8(m, 1H), 4.1(q, 2H), 14.0(br, 1H) |
| 10 | " | n-C₃H₇— | 119–110 | 0.9~1.2(m, 6H), 1.3~1.8(m, 4H), 1.45(s, 6H), 2.1(s, 3H), 2.3(s, 6H), 2.4~3.1(m, 8H), 3.4~3.7(m, 1H), 3.9~4.2(t, 2H), 14.1(br, 1H) |
| 11 | " | CH₂=CH—CH₂— | 85–87 | 1.0(t, 3H), 1.45(s, 6H), 1.65(m, 2H), 2.1(s, 3H), 2.2(s, 3H), 2.25(s, 3H), 2.45~2.7(m, 2H), 2.9~3.4(m, 6H), 3.75~3.9(m, 1H), 4.55(d, 2H), 5.3~5.45(m, 2H), 5.9~6.1(m, 1H), 15.08(br, 1H) |
| 12 | " | CH₂—C(Cl)=CH₂— | 105–107 | 1.0(t, 3H), 1.4(s, 6H), 1.5(m, 2H), 2.1(s, 3H), 2.3(s, 6H), 2.4~3.3(m, 8H), 3.4~3.9(m, 1H), 4.6(s, 2H), 5.5(s, 2H), 14.1(br, 1H) |
| 13 | " | ClCH=CH—CH₂— | 107–108 | 1.0(t, 3H), 1.45(s, 6H), 1.6(m, 2H), 2.1(s, 3H), 2.3(s, 6H), 2.5~3.2(m, 8H), 3.6~3.9(m, 1H), 4.5~4.8(2d, 2H), 5.9~6.4(m, 2H), 14.0(br, 1H) |
| 14 | n-C₃H₇— | 4-Cl-C₆H₄-CH₂— | 124–126 | 1.0(t, 3H), 1.45(s, 6H), 1.6(m, 2H), 2.1(s, 3H), 2.3(s, 6H), 2.5~3.2(m, 8H), 3.6~3.8(m, 1H), 5.1(s, 2H), 7.4(s, 4H), 14.0(br, 1H) |
| 15 | C₂H₅— | CH≡C—CH₂— | 136 | 1.0(t, 3H), 1.5(s, 6H), 2.1(s, 3H), 2.25(2s, 6H), 2.45~2.7(m, 3H), 2.8~3.4(m, 6H), 3.75~3.95(m, 1H), 4.55(d, 2H), 14.8(br, 1H) |
| 16 | " | cyclopropyl-CH₂— | | 0.35(m, 2H), 0.65(m, 2H), 1.2(m, 4H), 1.5(s, 6H), 2.1(s, 3H), 2.25(2s, 6H), 2.45~2.7(m, 2H), 2.9~3.4(m, 6H), 3.8~3.9(m, 1H), 3.9(d, 2H), 14.9(br, 1H) |
| 17 | C₂H₅— | CH₃—CH₂CH(CH₃)— | | 0.9(t, 3H), 1.15~1.3(2t, 6H), 1.48(s, 6H), 1.7(m, 2H), 2.1(s, 3H), 2.2~2.3(2s, 6H), 2.5~2.7(m, 2H), 2.9~3.3(6H), 3.8(m, 1H), 4.1(m, 1H), 15.0(br, 1H) |
| 18 | n-C₃H₇— | CH≡C—CH₂— | | 1.0(t, 3H), 1.5(s, 6H), 1.6(m, 2H), 2.1(s, 3H), |

TABLE 1-continued (I-a)

[Structure: cyclohexanone derivative with NOR³, R², OH, and substituted phenyl group]

| Compound No. | R² | R³ | m.p. (°C.) | ¹H NMR (CDCl₃, δ in ppm) |
|---|---|---|---|---|
| 19 | " | △—CH₂— | | 2.2~2.3(2s, 6H), 2.45~2.7(m, 3H), 2.8~3.35(m, 6H), 3.75~3.9(m, 1H), 4.7(d, 2H), 13.8(br, 1H) 0.4(m, 2H), 0.6(m, 2H), 1.0(t, 3H), 1.2(m, 1H), 1.45(s, 6H), 1.6(m, 2H), 2.1(s, 3H), 2.25(2s, 6H), 2.6~2.7(m, 2H), 2.9~3.4(6H), 3.8(m, 1H), 3.9(d, 2H), 14.8(br, 1H) |
| 20 | " | (CH₃CH₂)₂CH— | | 0.9~1.1(m, 9H), 1.5(s, 6H), 1.55~1.75(m, 6H), 2.1(s, 3H), 2.2~2.3(2s, 6H), 2.4~2.7(m, 2H), 2.9~3.3(m, 6H), 3.75~4.0(m, 2H), 15.0(br, 1H) |
| 21 | n-C₃H₇— | CH₃<br>\|<br>CH₃CH₂CH— | oil | 0.85~1.1(m, 6H), 1.15~1.25(m, 3H), 1.5(s, 6H), 1.6~1.8(m, 4H), 2.15(s, 3H), 2.2~2.3(2s, 6H), 2.4~2.8(m, 2H), 2.9~3.4(m, 6H), 3.8~4.0(m, 1H), 4.05~4.2(m, 1H), 14.5(br, 1H) |
| 22 | " | CH₃SCH₂— | | 1.0(t, 3H), 1.5(s, 6H), 1.65(m, 2H), 2.1(s, 3H), 2.2~2.3(3s, 9H), 2.5~2.7(m, 2H), 2.9~3.4(m, 6H), 3.8~4.0(m, 1H), 5.15(s, 2H), 14.2(br, 1H) |
| 23 | " | CH₃SCH₂CH₂— | 93–95 | 1.0(t, 3H), 1.5(s, 6H), 1.6~1.7(m, 2H), 2.1~2.3(4s, 12H), 2.45~2.7(m, 2H), 2.8~3.4(m, 8H), 3.75~3.9(m, 1H), 4.25(t, 2H), 14.0(br, 1H) |
| 24 | n-C₃H₇— | HOCH₂CH₂— | oil | 1.0(t, 3H), 1.45(s, 6H), 1.65(m, 2H), 2.1~2.3(3s, 9H), 2.5~2.7(m, 2H), 2.9~3.3(m, 6H), 3.7~3.9(m, 1H), 3.9~4.0(m, 2H), 4.25(m, 2H), 14.2(br, 1H) |
| 25 | n-C₃H₇— | CH₃CH₂OCH₂CH₂— | | 1.0(t, 3H), 1.25(t, 3H), 1.5(s, 6H), 1.6~1.8(m, 2H), 2.1(s, 3H), 2.2~2.3(2s, 6H), 2.45~2.7(m, 2H), 2.9~3.3(m, 6H), 3.5~3.9(m, 5H), 4.25(m, 2H), 14.3(br, 1H) |
| 26 | C₂H₅— | (CH₃CH₂)₂CH— | | 0.9~1.1(m, 6H), 1.2(t, 3H), 1.5(s, 6H), 1.7(m, 4H), 2.15(s, 3H), 2.25(2s, 6H), 2.5~2.7(m, 2H), 2.9~3.4(m, 6H), 3.8~4.0(m, 2H), 14.9(br, 1H) |

TABLE 2

(I-b)

[Structure: cyclohexanone derivative with Cl-substituted phenyl, NOR³, R², OH]

| Compound No. | R² | R³ | m.p.(°C.) | ¹H NMR(CDCl₃, δ in ppm) |
|---|---|---|---|---|
| 27 | C₂H₅— | CH₃— | | 1.1(t, 3H), 1.5(s, 6H), 2.1(s, 3H), 2.3(s, 3H), 2.5~2.7(m, 2H), 2.8~3.1(m, 6H), 3.5~3.8(m, 1H), 3.9(s, 3H), 13.1(br, 1H) |
| 28 | C₂H₅— | CH₃CH₂— | | 1.1(m, 6H), 1.4(s, 6H), 2.1(s, 3H), 2.2(s, 3H), 2.3~2.6(m, 2H), 2.8~3.2(m, 6H), 3.5~3.8(m, 1H), 4.0(q, 2H), 13.2(br, 1H) |
| 29 | C₂H₅— | CH₂=CH—CH— | | 1.1(t, 3H), 1.5(s, 6H), 2.1(s, 3H), 2.2(s, 3H), |

TABLE 2-continued

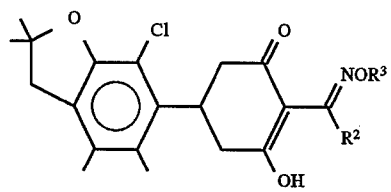
(I-b)

| Compound No. | $R^2$ | $R^3$ | m.p.(°C.) | $^1$H NMR(CDCl$_3$, δ in ppm) |
|---|---|---|---|---|
| 30 | $C_2H_5-$ | $ClCH=CH-CH_2-$ | | 2.5~3.1(m, 8H), 3.6~3.8(m, 1H), 4.6(d, 2H), 5.1~5.5(m, 2H), 5.6~5.9(m, 1H), 13.1(br, 1H) 1.1(t, 3H), 1.5(s, 6H), 2.1(s, 3H), 2.2(s, 3H), 2.5~3.3(m, 8H), 3.5~3.8(m, 1H), 4.3~4.8(m, 2H), 6.0~6.3(m, 2H), 13.4(br, 1H) |
| 31 | $C_2H_5-$ | $CH_2=\underset{\underset{Cl}{\mid}}{C}-CH_2-$ | 108–110 | 1.1(t, 3H), 1.5(s, 6H), 2.1(s, 3H), 2.2(s, 3H), 2.5~3.3(m, 8H), 3.5~3.8(m, 1H), 4.5(s, 2H), 5.4(s, 2H), 13.1(br, 1H) |
| 32 | $C_2H_5-$ | $CH_3-CH=CH-CH_2-$ | 86–87 | 1.2(t, 3H), 1.5(s, 6H), 1.8(d, 3H), 2.1(s, 3H), 2.2(s, 3H), 2.4~2.8(m, 2H), 3.0~3.8(m, 7H), 4.5(d, 2H), 5.5~5.8(m, 2H), 13.1(br, 1H) |
| 33 | $C_2H_5-$ | $CH_2=\underset{\underset{CH_3}{\mid}}{C}-CH_2-$ | 109–110 | 1.2(t, 3H), 1.5(s, 6H), 1.8(d, 3H), 2.1(s, 3H), 2.2(s, 3H), 2.4~2.7(m, 2H), 2.8~3.2(m, 6H), 3.5~3.8(m, 1H), 4.5(s, 2H), 5.0(s, 2H), 14.1(br, 1H) |
| 34 | $C_2H_5-$ | Cl-C$_6$H$_4$-CH$_2$- | 94–96 | 1.2(t, 3H), 1.5(s, 6H), 2.1(s, 3H), 2.2(s, 3H), 2.5~3.2(m, 8H), 3.4~3.8(m, 1H), 5.0(s, 2H), 7.0(s, 4H), 12.7(br, 1H) |
| 35 | $n$-$C_3H_7-$ | $CH_3-$ | | 1.0(t, 3H), 1.4(s, 6H), 1.5(m, 2H), 2.0(s, 3H), 2.1(s, 3H), 2.4~2.9(m, 2H), 3.0~3.5(m, 6H), 3.6~3.8(m, 1H), 3.85(s, 3H), 13.1(br, 1H) |
| 36 | $n$-$C_3H_7-$ | $C_2H_5-$ | | 1.0(t, 3H), 1.2(t, 3H), 1.4(s, 6H), 1.5(m, 2H), 2.0(s, 3H), 2.2(s, 3H), 2.3~2.8(m, 2H), 3.0~3.7(m, 7H), 4.1(q, 2H), 13.1(br, 1H) |
| 37 | $n$-$C_3H_7-$ | $CH_2=CH-CH_2-$ | | 1.0(t, 3H), 1.4(m, 2H), 1.5(s, 6H), 2.1(s, 3H), 2.2(s, 3H), 2.3~3.0(m, 6H), 3.3~3.8(m, 3H), 4.3~4.5(d, 2H), 5.1~5.4(m, 2H), 5.7~6.0(m, 1H), 13.2(br, 1H) |
| 38 | $n$-$C_3H_7-$ | $ClCH=CH-CH_2-$ | 99–100 | 1.1(t, 3H), 1.3(m, 2H), 1.5(s, 6H), 2.0(s, 3H), 2.1(s, 3H), 2.5~3.1(m, 6H), 3.4~3.8(m, 3H), 5.0(2d, 2H), 6.2~6.6(m, 2H), 13.1(br, 1H) |
| 39 | $n$-$C_3H_7-$ | $CH_2=\underset{\underset{Cl}{\mid}}{C}-CH_2-$ | | 1.0(t, 3H), 1.3(m, 2H), 1.5(s, 6H), 2.0(s, 3H), 2.1(s, 3H), 2.3~3.1(m, 6H), 3.4~3.8(m, 3H), 4.5(s, 2H), 5.5(s, 2H), 12.9(br, 1H) |
| 40 | $n$-$C_3H_7-$ | $CH_3-CH=CH-CH_2-$ | | 1.0(t, 3H), 1.2(m, 2H), 1.5(s, 6H), 1.7(d, 3H), 2.1(s, 3H), 2.2(s, 3H), 2.4~3.1(m, 6H), 3.3~3.7(m, 3H), 4.5(m, 2H), 5.7(m, 2H), 13.0(br, 1H) |
| 41 | $n$-$C_3H_7-$ | $CH_2=\underset{\underset{CH_3}{\mid}}{C}-CH_2-$ | 92 | 1.1(t, 3H), 1.3(m, 2H), 1.8(s, 6H), 1.8(s, 3H), 2.2(s, 3H), 2.25(s, 3H), 2.4~2.8(m, 2H), 2.9~3.2(m, 6H), 3.6~3.9(m, 1H), 4.5(s, 2H), 5.1(s, 2H), 12.9(br, 1H) |
| 42 | $n$-$C_3H_7-$ | Cl-C$_6$H$_4$-CH$_2$- | | 1.0(t, 3H), 1.3(m, 2H), 1.6(s, 6H), 2.2(s, 3H), 2.3(s, 3H), 2.5~3.1(m, 8H), 3.5~4.1(m, 1H), 5.0(s, 2H), 7.4(s, 4H), 13.8(br, 1H) |
| 43 | $C_2H_5-$ | $CH\equiv C-CH_2-$ | foam | 1.1(t, 3H), 1.5(s, 6H), 2.1(s, 3H), 2.2(s, 3H), 2.3~2.6(m, 3H), 2.8~2.9(q, 2H), 3.0(s, 2H), 3.4~4.0(m, 3H), 4.65(d, 2H), 14.8(br, 1H) |

TABLE 2-continued (I-b)

| Compound No. | R² | R³ | m.p.(°C.) | ¹H NMR(CDCl₃, δ in ppm) |
|---|---|---|---|---|
| 44 | $C_2H_5-$ | cyclopropyl-CH₂- | | 0.3(m, 2H), 0.6(m, 2H), 1.2(m, 4H), 1.5(s, 6H), 2.1(s, 3H), 2.2(s, 3H), 2.4–2.6(m, 2H), 2.9–3.1(m, 6H), 3.5–3.8(m, 1H), 3.9(d, 2H), 15.0(br, 1H) |
| 45 | $C_2H_5-$ | CH₃<br>\|<br>CH₃CH₂—CH— | | 0.95(t, 3H), 1.2(t, 3H), 1.3(d, 3H), 1.5(s, 6H), 2.6–2.8(m, 2H), 2.15–2.2(2s, 6H), 2.35–2.6(m, 2H), 2.9–3.1(m, 6H), 3.7–3.8(m, 1H), 4.0–4.2(m, 1H), 14.1(br, 1H) |
| 46 | $n-C_3H_7-$ | CH≡C—CH₂— | 85–86 | 0.95(t, 3H), 1.5(s, 6H), 1.6(m, 2H), 2.1(s, 3H), 2.2(s, 3H), 2.3–2.6(m, 3H), 2.85(q, 2H), 3.0(s, 2H), 3.5–3.9(m, 3H), 4.65(d, 2H), 14.5(br, 1H) |
| 47 | $n-C_3H_7-$ | cyclopropyl-CH₂- | | 0.3(m, 2H), 0.6(m, 2H), 1.0(t, 3H), 1.2(m, 1H), 1.5(s, 6H), 1.65(m, 2H), 2.1(s, 3H), 2.2(s, 3H), 2.4–2.6(m, 2H), 2.9–3.1(m, 6H), 3.5–3.7(m, 1H), 3.9(d, 2H), 14.5(br, 1H) |
| 48 | $n-C_3H_7-$ | CH₃<br>\|<br>CH₃CH₂—CH— | oil | 0.9(t, 3H), 1.0(t, 3H), 1.3(d, 3H), 1.5(s, 6H), 1.6–1.8(m, 4H), 2.15–2.25(2s, 6H), 2.4–2.6(m, 2H), 2.9–3.1(m, 6H), 3.6–4.0(m, 1H), 4.1(m, 1H), 13.8(br, 1H) |

TABLE 3

(I-c)

| Compound No. | R² | R³ | m.p. (°C.) | ¹H NMR (CDCl₃, δ in ppm) |
|---|---|---|---|---|
| 49 | $C_2H_5-$ | $CH_3-$ | 141–142 | 1.1(t, 3H), 1.5(s, 6H), 2.2(s, 6H), 2.3(s, 3H), 2.35–2.55(m, 2H), 2.9(m, 4H), 3.2–3.4(m, 1H), 3.5–3.7(m, 2H), 3.9(s, 3H), 13.8(br, 1H) |
| 50 | $C_2H_5-$ | $C_2H_5-$ | 103 | 1.25(t, 3H), 1.35(t, 3H), 1.5(s, 6H), 2.2(s, 6H), 2.3(s, 3H), 2.45–2.55(m, 2H), 2.95–3.1(m, 4H), 3.3–3.5(m, 1H), 3.6–3.7(m, 2H), 4.2(q, 2H), 13.7(br, 1H) |
| 51 | $C_2H_5-$ | $CH_2=CH-CH_2-$ | 104–105 | 1.3(t, 3H), 1.5(s, 6H), 2.2(s, 6H), 2.3(s, 3H), 2.4–2.6(m, 2H), 3.0(m, 4H), 3.3–3.5(m, 1H), 3.6–3.8(m, 2H), 4.6(m, 2H), 5.3–5.5(m, 2H), 5.95–6.2(m, 1H), 13.8(br, 1H) |
| 52 | $C_2H_5-$ | Cl<br>\|<br>CH=CH—CH₂— | 120–122 | 1.2(t, 3H), 1.4(s, 6H), 2.1(s, 6H), 2.2(s, 3H), 2.3–2.5(m, 2H), 2.8–3.0(m, 4H), 3.2–3.4(m, 1H), 3.5–3.7(m, 2H), 4.5(d, 1H), 4.75(d, 1H), 6.0–6.4(m, 2H), 13.7(br, 1H) |
| 53 | $C_2H_5-$ | Cl<br>\|<br>CH₂=C—CH₂— | 124–125 | 1.1(t, 3H), 1.4(d, 6H), 2.1(s, 6H), 2.2(s, 3H), 2.3–2.5(m, 2H), 2.9(m, 4H), 3.2–3.4(m, 1H), 3.5–3.7(m, 2H), 4.6(s, 2H), 5.5(s, 2H), 13.8(br, 1H) |

TABLE 3-continued

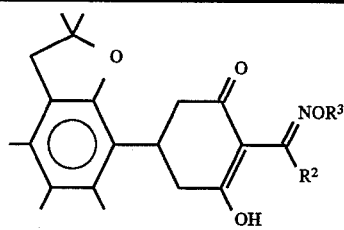

(I-c)

| Compound No. | $R^2$ | $R^3$ | m.p. (°C.) | $^1$H NMR (CDCl$_3$, δ in ppm) |
|---|---|---|---|---|
| 54 | C$_2$H$_5$— | CH$_2$=C(CH$_3$)—CH$_2$— | 100 | 1.25(t, 3H), 1.5(s, 6H), 1.8(s, 3H), 2.2(s, 6H), 2.3(s, 3H), 2.3~2.5(m, 2H), 2.9~3.1(m, 4H), 3.2~3.4(m, 1H), 3.5~3.7(m, 2H), 4.5(s, 2H), 5.1(s, 2H), 13.7(br, 1H) |
| 55 | C$_2$H$_5$— | CH$_3$—CH=CH—CH$_2$— | 110 | 1.25(t, 3H), 1.5(s, 6H), 1.8(d, 3H), 2.2(s, 6H), 2.3(s, 3H), 2.4~2.6(m, 2H), 2.9~3.1(m, 4H), 3.25~3.5(m, 1H), 3.6~3.8(m, 2H), 4.5(d, 2H), 5.5~6.0(m, 2H), 13.8(br, 1H) |
| 56 | C$_2$H$_5$— | (CH$_3$CH$_2$)$_2$CH— | oil | 1.0(m, 6H), 1.25(m, 3H), 1.5(s, 6H), 1.7(m, 4H), 2.2(s, 6H), 2.3(s, 3H), 2.4~2.7(m, 2H), 2.9~3.1(m, 4H), 3.3~3.8(m, 3H), 3.9(m, 1H), 14.0(br, 1H) |
| 57 | n-C$_3$H$_7$— | CH$_3$— | 141–142 | 1.0(t, 3H), 1.5(s, 6H), 1.6~1.7(q, 2H), 2.2(s, 6H), 2.3(s, 3H), 2.4~2.6(m, 2H), 2.9~3.0(m, 4H), 3.25~3.45(m, 1H), 3.5~3.7(m, 2H), 3.9(s, 3H), 13.8(br, 1H) |
| 58 | n-C$_3$H$_7$— | CH$_3$CH$_2$— | 104–105 | 1.1(t, 3H), 1.4(t, 3H), 1.5(s, 6H), 1.6~1.75(q, 2H), 2.2(s, 6H), 2.3(s, 3H), 2.4~2.6(m, 2H), 2.9~3.1(m, 4H), 3.3~3.5(m, 1H), 3.6~3.7(m, 2H), 4.1~4.3(q, 2H), 13.5(br, 1H) |
| 59 | n-C$_3$H$_7$— | CH$_2$=CH—CH$_2$— | | 1.1(t, 3H), 1.5(s, 6H), 1.7(q, 2H), 2.2(s, 6H), 2.3(s, 3H), 2.4~2.6(m, 2H), 2.9~3.1(m, 4H), 3.25~3.45(m, 1H), 3.55~3.75(m, 2H), 4.6(d, 2H), 5.3~5.5(m, 2H), 5.95~6.2(m, 1H), 13.7(br, 1H) |
| 60 | n-C$_3$H$_7$— | ClCH=CH—CH$_2$— | | 1.1(t, 3H), 1.5(s, 6H), 1.7(q, 2H), 2.2(s, 6H), 2.3(s, 3H), 2.4~2.6(m, 2H), 2.9~3.1(m, 4H), 3.25~3.45(m, 1H), 3.55~3.75(m, 2H), 4.5(d, 1H), 4.75(d, 1H), 6.0~6.4(m, 2H), 13.8(br, 1H) |
| 61 | n-C$_3$H$_7$— | CH$_2$=C(Cl)—CH$_2$— | 131–133 | 1.1(t, 3H), 1.5(s, 6H), 1.7(q, 2H), 2.2(s, 6H), 2.3(s, 3H), 2.5(m, 2H), 2.9~3.2(m, 4H), 3.25~3.45(m, 1H), 3.5~3.75(m, 2H), 4.6(s, 2H), 5.5(m, 2H), 13.7(br, 1H) |
| 62 | n-C$_3$H$_7$— | CH$_2$=C(CH$_3$)—CH$_2$— | 94 | 1.1(t, 3H), 1.5(s, 6H), 1.7(q, 2H), 1.8(s, 3H), 2.2(s, 6H), 2.3(s, 3H), 2.4~2.6(m, 2H), 2.9~3.1(m, 4H), 3.25~3.4(m, 1H), 3.5~3.7(m, 2H), 4.5(s, 2H), 5.1(s, 2H), 13.8(br, 1H) |
| 63 | n-C$_3$H$_7$— | CH$_3$CH=CH—CH$_2$— | 109 | 1.1(t, 3H), 1.5(s, 6H), 1.7(q, 2H), 1.8(d, 3H), 2.2(s, 6H), 2.3(s, 3H), 2.4~2.6(m, 2H), 2.9~3.0(m, 4H), 3.25~3.45(m, 1H), 3.55~3.7(m, 2H), 4.5(d, 2H), 5.6~6.0(m, 2H), 13.8(br, 1H) |
| 64 | n-C$_3$H$_7$— | CH$_2$=CH—CH(CH$_3$)— | 83 | 1.0(t, 3H), 1.45(3s, 9H), 1.7(q, 2H), 2.15(s, 6H), 2.25(s, 6H), 2.4~2.7(m, 2H), 2.9(s, 2H), 3.05(t, 2H), 3.25~3.5(m, 1H), 3.6~3.7(m, 2H), 4.8(m, 1H), 5.2(m, 2H), 6.0(m, 1H), 13.7(s, 1H) |
| 65 | n-C$_3$H$_7$— | CH≡C—CH$_2$— | 120 | 1.0(t, 3H), 1.45(s, 6H), 1.65(q, 2H), 2.15(s, 6H), 2.25(s, 3H), 2.3~2.6(m, 3H), 2.7~3.0(m, 4H), 3.2~3.7(m, 3H), 4.65(d, 2H), 14.1(br, 1H) |
| 66 | C$_2$H$_5$— | CH≡C—CH$_2$— | 138 | 1.2(t, 3H), 1.5(s, 6H), 2.2(s, 6H), 2.25(s, 3H), 2.4~2.6(m, 3H), 2.9~3.1(m, 4H), |

TABLE 3-continued

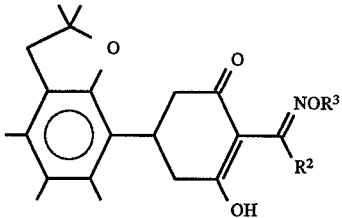
(I-c)

| Compound No. | R² | R³ | m.p. (°C.) | ¹H NMR (CDCl₃, δ in ppm) |
|---|---|---|---|---|
| | | | | 3.3~3.8(m, 3H), 4.7(d, 2H), 14.2(br, 1H) |
| 67 | $C_2H_5-$ | 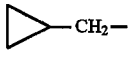 | | 0.35(m, 2H), 0.65(m, 2H), 1.2(m, 1H), 1.25(t, 3H), 1.5(s, 6H), 2.15(s, 6H), 2.25(s, 3H), 2.3~2.6(m, 2H), 2.9~3.1(m, 4H), 3.3~3.7(m, 3H), 3.9(d, 2H), 13.8(br, 1H) |
| 68 | $n-C_3H_7-$ | 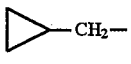 | | 0.35(m, 2H), 0.65(m, 2H), 1.05(t, 3H), 1.2(m, 1H), 1.5(s, 6H), 1.7(q, 2H), 2.2(s, 6H), 2.25(s, 3H), 2.3~2.6(m, 2H), 2.9~3.1(m, 4H), 3.3~3.7(m, 3H), 3.9(d, 2H), 14.0(br, 1H) |
| 69 | $n-C_3H_7-$ | $(CH_3CH_2)_2CH-$ | 92 | 1.0(m, 9H), 1.5(s, 6H), 1.7(m, 6H), 2.2(s, 6H), 2.25(s, 3H), 2.4~2.6(m, 2H), 2.9~3.1(m, 4H), 3.4~3.8(m, 3H), 3.9(m, 1H), 14.0(br, 1H) |
| 70 | $C_2H_5-$ | $CH_3CH_2-\overset{CH_3}{\underset{\|}{CH}}-$ | | 1.0(t, 3H), 1.25(t, 3H), 1.3(d, 2H), 1.5(s, 6H), 1.65(m, 2H), 2.2(s, 6H), 2.25(s, 3H), 2.3~2.5(m, 2H), 2.9~3.1(m, 4H), 3.4~3.6(m, 3H), 4.1(m, 1H), 13.8(br, 1H) |
| 71 | $n-C_3H_7-$ | $CH_3CH_2-\overset{CH_3}{\underset{\|}{CH}}-$ | | 1.0(m, 6H), 1.3(d, 3H), 1.5(s, 6H), 1.6~1.9(m, 4H), 2.2(s, 6H), 2.3(s, 3H), 2.4~2.6(m, 4H), 2.9~3.1(m, 4H), 3.4~3.8(m, 4H), 4.1(m, 1H), 14.0(br, 1H) |

TABLE 4

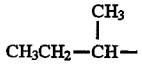
(I-d)

| Compound No. | R² | R³ | m.p. (°C.) | ¹H NMR (CDCl₃, δ in ppm) |
|---|---|---|---|---|
| 72 | $C_2H_5-$ | $CH_3-$ | oil | 1.2(t, 3H), 1.45(s, 6H), 2.1(s, 3H), 2.2(s, 6H), 2.4~2.7(m, 2H), 2.85~3.0(m, 5H), 3.0~3.4(m, 2H), 3.9(s, 2H) |
| 73 | $C_2H_5-$ | $CH_3CH_2-$ | oil | 1.2(t, 3H), 1.35(t, 3H), 1.48(s, 6H), 2.15(s, 3H), 2.25(s, 6H), 2.45~2.7(m, 2H), 2.9~3.05(m, 4H), 3.1~3.4(m, 2H), 3.8~4.0(m, 1H), 4.05~4.2(q, 2H), 14.1(br, 1H) |
| 74 | $C_2H_5-$ | $CH_2=CH-CH_2-$ | oil | 1.15(t, 3H), 1.45(s, 6H), 2.1(s, 3H), 2.2(s, 6H), 2.4~2.7(m, 2H), 2.75~3.0(m, 4H), 3.05~3.3(m, 2H), 3.75~4.0(m, 1H), 4.5(m, 2H), 5.25~5.4(m, 2H), 5.85~6.1(m, 1H), 13.9(br, 1H) |
| 75 | $C_2H_5-$ | $CH_2=\overset{Cl}{\underset{\|}{C}}-CH_2-$ | oil | 1.2(t, 3H), 1.45(s, 6H), 2.1(s, 3H), 2.2(s, 6H), 2.4~2.7(m, 2H), 2.9~3.4(m, 6H), 3.8~4.1(m, 1H), 4.65(s, 2H), 5.5(s, 2H), 14.0(br, 1H) |
| 76 | $C_2H_5-$ | $CH\equiv C-CH_2-$ | oil | 1.2(t, 3H), 1.4(s, 6H), 2.1(s, 3H), 2.2(s, 6H), 2.4~2.7(m, 3H), 2.75~3.35(m, 6H), 3.8~4.1(m, 1H), 4.6(s, 2H) |

TABLE 4-continued

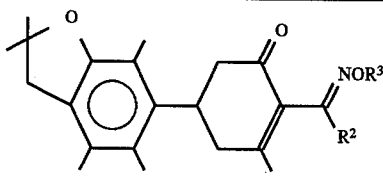

(I-d)

| Compound No. | R² | R³ | m.p. (°C.) | ¹H NMR (CDCl₃, δ in ppm) |
|---|---|---|---|---|
| 77 | $C_2H_5-$ | 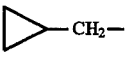—CH₂— | oil | 0.3(m, 2H), 0.65(m, 2H), 0.85(m, 1H), 1.2(t, 3H), 1.45(s, 6H), 2.15(s, 3H), 2.25(s, 6H), 2.4–2.7(m, 2H), 2.9–3.4(m, 6H), 3.85–3.9(m, 3H), 14.2(br, 1H) |
| 78 | $n-C_3H_7-$ | $CH_3-$ | oil | 1.0(t, 3H), 1.45(s, 6H), 1.6(m, 2H), 2.1(s, 3H), 2.2(s, 6H), 2.4–2.7(m, 2H), 2.9(t, 2H), 2.95(s, 2H), 3.0–3.4(m, 2H), 3.8–3.9(m, 4H), 14.8(br, 1H) |
| 79 | $n-C_3H_7-$ | $CH_3-CH_2-$ | oil | 1.0(t, 3H), 1.3(t, 3H), 1.45(s, 6H), 1.65(m, 2H), 2.1(s, 3H), 2.2(s, 6H), 2.4–2.7(m, 2H), 2.85–3.0(m, 4H), 3.0–3.4(m, 2H), 3.8–4.0(m, 1H), 4.1–4.2(q, 2H), 14.2(br, 1H) |
| 80 | $n-C_3H_7-$ | $CH_2=CH-CH_2-$ | oil | 1.0(t, 3H), 1.45(s, 6H), 1.6(m, 2H), 2.1(s, 3H), 2.2(s, 6H), 2.4–2.7(m, 2H), 2.85–3.0(m, 4H), 3.0–3.4(m, 2H), 3.8–4.0(m, 1H), 4.5(d, 2H), 5.4(m, 2H), 6.0(m, 1H), 15.2(br, 1H) |
| 81 | $n-C_3H_7-$ | $\begin{array}{c} Cl \\ | \\ CH_2=C-CH_2- \end{array}$ | oil | 1.0(t, 3H), 1.45(s, 6H), 1.6(m, 2H), 2.1(s, 3H), 2.2(s, 6H), 2.4–2.7(m, 2H), 2.85–3.4(m, 6H), 3.8–4.0(m, 1H), 4.6(s, 2H), 5.5(m, 2H), 14.8(br, 1H) |
| 82 | $n-C_3H_7-$ | $CH\equiv C-CH_2-$ | oil | 1.0(t, 3H), 1.45(s, 6H), 1.6(m, 2H), 2.1(s, 3H), 2.2(s, 6H), 2.4–2.7(m, 3H), 2.8–3.4(m, 6H), 3.8–4.1(m, 1H), 4.7(d, 2H), 14.9(br, 1H) |
| 83 | $n-C_3H_7-$ | 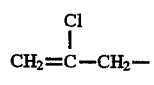—CH₂— | oil | 0.3(m, 2H), 0.6(m, 2H), 1.0(t, 3H), 1.2(m, 1H), 1.45(s, 6H), 1.6(m, 2H), 2.1(s, 3H), 2.2(s, 6H), 2.4–2.7(m, 2H), 2.9–3.4(m, 6H), 3.8–4.1(m, 3H), 14.5(br, 1H) |

Preparation of the present compounds of formula (I) and the intermediates shown in the chemical equations is illustrated further in the following examples.

EXAMPLE 1

2-[1-(Allyloxyimino)butyryl]-5-(2,3-dihydro-2,2,4,6,7-pentamethylbenzofuran-5-yl)-3-hydroxycyclohex-2-en-1-one (11)

i) Methallyl 2,3,5-trimethylphenyl ether.

To a solution of 100 g of 2,3,5-trimethylphenol in 500 ml of acetone was added 75 g of anhydrous potassium carbonate. After refluxing for 45 hours, the reaction mixture was filtered, concentrated under reduced pressure and diluted with diethyl ether. The mixture was extracted three times with 300 ml of 20% aqueous solution of sodium hydroxide. The combined organic extracts were washed with water, dried over anhydrous magnesium sulfate, filtered and concentrated under the reduced pressure to afford the compound of methallyl 2,3,5-trimethylphenyl ether(105 g, yield 75%) as colorless liquid.

b.p.: 75°–77.5° C. /0.15 torr.

¹H NMR (CDCl₃): δ1.7 (s, 3H), 2.2–2.3 (3s, 9H), 4.4 (s, 2H), 5.0–5.2 (d, 2H), 6.5–6.6 (d, 2H).

ii) 2,3-Dihydro-2,2,4,6,7-pentamethylbenzofuran.

To a solution of 71.5 g of methallyl 2,3,5-trimethylphenyl ether in 350 ml of absolute dichloromethane at −70° C. was added 50 g of AlCl₃ under a current of nitrogen gas. After stirring at −70° C. for 1 hour, the reaction mixture was added 500 g of ice-water and stirred for 20 minutes. Thereafter the aqueous layer was extracted with dichloromethane. The combined organic extracts were washed with water, dried over anhydrous magnesium sulfate and concentrated under reduced pressure to afford 62.5 g of 2,3-dihydro-2,2,4,6,7-pentamethylbenzofuran as a white solid.

m.p.: 47° C.

¹H NMR (CDCl₃): δ1.5 (s, 6H), 2.1–2.3 (3s, 9H), 2.9 (s, 2H), 6.5 (s, 1H).

iii) 2,3-Dihydro-2,2,4,6,7-pentamethylbenzofuran-5-carboxyaldehyde.

To a solution of 40.6 g of the 2,3-dihydro-2,2,4,6,7-pentamethylbenzofuran in 400 ml of absolute dichloromethane was added 17.9 ml of titanium chloride (IV) and 20 ml of α,α-dichloromethyl methyl ether at 0° C. under a current of nitrogen gas. With stirring at room temperature for 45 minutes and refluxing for 15 minutes the reaction mixture was quenched with 30 ml of ice water and the aqueous layer was extracted with dichloromethane. The combined organic extracts were dried over anhydrous magnesium sulfate, filtered and concentrated under reduced pressure to afford 44 g of 2,3-dihydro-2,2,4,6,7-pentamethylbenzofuran-5-carboxyaldehyde as a needle shape crystal.

m.p.: 101°–102° C.

¹H NMR (CDCl₃): δ1.5 (s, 6H), 2.2 (s, 3H), 2.5 (s, 3H), 2.6 (s, 3H), 3.05 (s, 2H), 10.6 (s, 1H).

iv) 4-(2,3-Dihydro-2,2,4,6,7-pentamethylbenzofuran-5-yl)-3-buten-2-one.

To a solution of 30 g of the 2,3-dihydro-2,2,4,6,7-pentamethylbenzofuran-5-carboxyaldehyde in 100 ml of acetone was added 50 ml of distilled water and 60 ml of aqueous solution of sodium hydroxide. After refluxing for 20 hours, the reaction mixture was quenched by 2N aqueous solution of hydrochloric acid and the aqueous layer was extracted with diethyl ether. The combined organic extracts were dried over anhydrous magnesium sulfate, filtered and concentrated under reduced pressure to afford 27 g of 4-(2,3-dihydro-2,2,4,6,7-pentamethylbenzofuran-5-yl)-3-buten-2-one as a yellow solid.

m.p.: 86°–87° C.

¹H NMR (CDCl₃): δ1.5 (s, 6H), 2.1–2.3 (3s, 9H), 2.4 (s, 3H), 3.0 (s, 2H), 6.1–6.4 (d, 1H), 7.6–7.9 (d, 1H).

v) 5-(2,3-Dihydro-2,2,4,6,7-pentamethylbenzofuran-5-yl) cyclohexane-1,3-dione.

To a solution of 0.86 g of sodium in 37 ml of absolute methanol was added 5.6 ml of diethyl malonate. After stirring for 20 minutes, the mixture was added 8 g of the 4-(2,3-dihydro-2,2,4,6,7-pentamethylbenzofuran-5- yl)-3-buten-2-one in 15 ml of absolute methanol, refluxed for 4 hours and then added 75 g of 6% aqueous solution of sodium hydroxide and refluxed for 4 hours. The reaction mixture was cooled to room temperature and washed three times with 50 ml of diethyl ether. 2N aqueous solution of hydrochloric acid was added drop wise into the aqueous layer until the bubble of carbon dioxide ceased. Solid was dissolved in ethyl acetate and washed with water. The combined organic layer was dried over anhydrous magnesium sulfate and concentrated under reduced pressure to afford 6.36 g of 5-(2,3-dihydro-2,2,4,6,7-pentamethylbenzofuran-5-yl) cyclohexane-1,3-dione as a yellow solid.

m.p.: 171° C.

¹H NMR (CDCl₃): δ1.75 (s, 6H), 2.1–2.3 (3s, 9H), 2.4–2.6 (m, 2H), 3.0 (s, 2H), 3.05–3.3 (m, 2H), 3.8–4.0 (m, 1H), 5.7 (s, 1H).

vi) 2-Butyryl-5-(2,3-dihydro-2,2,4,6,7-pentamethylbenzofuran-5-yl)-3-hydroxycy-clohex-2-en-1-one.

To a solution of 3.18 g of the 5-(2,3-dihydro-2,2,4,6,7-pentamethylbenzofuran-5-yl)cyclohexane-1,3-dione in 50 ml of absolute toluene was added 6.93 ml of anhydrous butyric acid and refluxed for 4 hours. The reaction mixture was cooled to room temperature and concentrated under reduced pressure to afford an oily residue. To the solution of the residue in 50 ml of absolute toluene was added 0.26 g of 4-dimethylaminopyridine. After refluxing 8 hours, the reaction mixture was cooled to room temperature and concentrated under reduced pressure to afford a crude product. Final purification was carried by silica-gel column chromatography to afford 3.8 g of 2-butyryl-5-(2,3-dihydro-2,2,4,6,7-pentamethylbenzofuran-5-yl)-3-hydroxycyclohex-2-en-1-one as a yellow solid.

m.p.: 83° C.

¹H NMR(CDCl₃): δ0.9–1.2 (m, 3H), 1.5 (s, 6H), 1.65 (m, 2H), 2.1–2.3 (3s, 9H), 2.4–2.6 (m, 2H), 2.7–2.9 (m, 4H), 3.0–3.4 (m, 2H), 3.7–3.9 (m, 1H), 14.6 (br, 1H).

vii) 5-(2,3-Dihydro-2,2,4,6,7-pentamethylbenzofuran-5-yl)-2-[1-(allyloxyimino) butyryl]-3-hydroxycyclohex-2-en-1-one.

To a solution 2.5 g of the 2-butyryl-5-(2,3-dihydro-2,2,4,6,7-pentamethyl-benzofuran-5-yl)-3-hydroxycyclohex-2-en-1-one in 35 ml of ethanol was added 1.1 g of sodium acetate and 0.82 g of allylhydroxylamine hydrochloride. After stirring at room temperature for 4 hours, the reaction mixture was quenched with 100 ml water and extracted three times with 50 ml of diethyl ether. The combined organic extracts were dried over anhydrous magnesium sulfate, filtered and concentrated under the reduced pressure to afford a crude product. Final purification was carried by recrystallization to afford 2.12 g of 5-(2,3-dihydro-2,2,4,6,7-pentamethylbenzofuran-5-yl)-2-[1-(allyloxyimino)butyryl]-3-hydroxycyclohex-2-en-1-one as a white solid.

m.p.: 85°–87° C.

¹H NMR (CDCl₃): δ1.0 (t,3H), 1.45 (s, 6H), 1.65 (m, 2H), 2.1 (s, 3H), 2.2 (s, 3H), 2.25 (s, 3H), 2.45–2.7 (m, 2H), 2.9–3.4 (m, 6H), 3.75–3.9 (m, 1H), 4.55 (d, 2H), 5.3–5.45 (m, 2H), 5.9–6.1 (m, 1H), 15.08 (br, 1H).

EXAMPLE 2

5-(7-Chloro-2,3-dihydro-2,2,4,5-tetramethylbenzofuran-6-yl)-2-[1-(ethoxyimino) propyl]-3-hydroxycyclohex-2-en-1-one (28)

i) Methallyl 2-chloro-4,5-dimethylphenyl ether.

To a solution 23.5 g of 2-chloro-4,5-dimethylphenol in 100 ml of acetone was added 16 g of anhydrous potassium carbonate and 22.2 ml of 3-chloro-2-methyl-propene. After refluxing for 24 hours, the reaction mixture was filtered, concentrated under reduced pressure and diluted with 100 ml of diethyl ether. The mixture was extracted three times with 50 ml of 10% aqueous solution of sodium hydroxide. The combined organic extracts were washed with water, dried over anhydrous magnesium sulfate, filtered and concentrated under the reduced pressure to afford a crude product. Final purification was carried by silica-gel column chromatography to afford 23.8 g of methally 2-chloro-4,5-dimethylphenyl ether.

¹H NMR (CDCl₃): δ1.8 (s, 3H), 2.1–2.2 (2d, 6H), 4.4 (s, 2H), 5.0–5.2 (d, 2H), 6.7 (s, 1H), 7.1 (s, 1H).

ii) 7-Chloro-2,3-dihydro-2,2,4,5-tetramethylbenzofuran.

To a solution of 23.8 g of the methally 2-chloro-4,5-dimethylphenyl ether in 200 ml absolute dichloromethane at −70° C. was added 10 g of AlCl₃ under a current of nitrogen gas. After stirring and warming to the room temperature over a period of 1 hour, the reaction mixture was added 200 ml of ice-water and the aqueous layer was extracted with dichloromethane. The organic extract was washed with water, dried over anhydrous magnesium sulfate and concentrated under reduced pressure to afford a crude product. Final purification was carried by silica-gel column chromatography to afford 20 g of 7-chloro-2,3-dihydro-2,2,4,5-tetramethylbenzofuran as yellow oil.

¹H NMR (CDCl₃): δ1.5 (s, 6H), 2.05 (s, 3H), 2.25 (s, 3H), 2.9 (s, 2H), 6.8 (s, 1H).

iii) 7-Chloro-2,3-dihydro-2,2,4,5-tetramethylbenzofuran-6-carboxaldehyde.

To a solution of 20 g of the 7-chloro-2,3-dihydro-2,2,4,5-tetramethylbenzofuran in 200 ml of absolute dichloromethane was added 27.3 ml of titanium chloride(IV) and 18.75 ml of α,α-dichloromethyl methyl ether at 0° C. With stirring at room temperature for 45 minutes and refluxing for 15 minutes, the reaction mixture was quenched with 200 ml of ice-water and stirred for 30 minutes and the aqueous layer was extracted with dichloromethane. The combined organic extracts were dried over anhydrous magnesium sulfate, filtered and concentrated under reduced pressure to afford a crude product. Final purification was carried by silica-gel column chromatography to afford 14 g of 7-chloro-2,3-dihydro-2,2,4,5-tetramethylbenzofuran-6-carboxaldehyde.

¹H NMR (CDCl₃): δ1.5 (s, 6H), 2.1 (s, 3H), 2.35 (s, 3H), 3.05 (s, 2H), 10.5 (s, 1H)

iv) 4-(7-Chloro-2,3-dihydro-2,2,4,5-tetramethylbenzofuran-6-yl)-3-buten-2-one.

To a solution of 12 g of the 7-chloro-2,3-dihydro-2,2,4,5-tetramethyl-benzo-furan-6-carboxaldehyde in 25 ml of acetone was added 8 ml of water and 2 ml of 10% aqueous solution of sodium hydroxide. After refluxing at 40° C. for 15 hours, the reaction mixture was quenched with 2N aqueous solution of hydrochloric acid and the aqueous layer was extracted with diethyl ether. The combined organic extracts were dried over anhydrous magnesium sulfate, filtered and concentrated under reduced pressure to afford a crude product. Final purification was carried by silica-gel column chromatography to afford 10 g of 4-(7-chloro-2,3-dihydro-2,2,4,5-tetramethyl-benzofuran-6-yl)-3-buten-2-one.

¹H NMR (CDCl₃): δ1.5 (s, 6H), 2.1 (s, 3H), 2.2 (s, 3H), 2.35 (s, 3H), 3.0 (s, 2H), 6.1–6.4 (d, 1H), 7.3–7.6 (d, 1H).

v) 5-(7-Chloro-2,3-dihydro-2,2,4,5-tetramethylbenzofuran-6-yl)-3-hydroxycy-clohex-2-ene-1-one.

To a solution of 1.0 g of sodium in 30 ml of absolute methanol was added 6.5 ml of diethyl malonate and 10 g of the 4-(7-chloro-2,3-dihydro-2,2,4,5-tetramethyl-benzofuran-6-yl)-3-buten-2-one in 20 ml of absolute methanol, and refluxed for 4 hours. The reaction mixture was added 100 ml of water and concentrated under reduced pressure and then added 17 g of 20% aqueous solution of sodium hydroxide. After refluxing 1 hour, the reaction mixture was cooled to room temperature and washed with benzene. Concentrated hydrochloric acid was added dropwise into the aqueous layer until the bubble of carbon dioxide ceased. And then, solid was dissolved in ethyl acetate and washed with water. The combined organic layer was dried over anhydrous magnesium sulfate and concentrated under reduced pressure to afford 11.8 g of 5-(7-chloro-2,3-dihydro-2,2,4,5-tetramethylbenzofuran-6-yl)-3-hydroxycyclohex-2-en-1-one.

¹H NMR (DMSO-d₆): δ1.4 (s, 6H), 2.1 (s, 3H), 2.2 (s, 3H), 2.3 (m, 2H), 3.0 (s, 2H), 3.05–3.2 (m, 2H), 3.6–3.8 (m, 1H), 5.3 (s, 1H).

vi) 5-(7-Chloro-2,3-dihydro-2,2,4,5-tetramethylbenzofuran-6-yl)-2-propionyl-3-hydroxycyclohex-2-en-1-one.

To a solution of 5.9 g of the 5-(7-chloro-2,3-dihydro-2,2,4,5-tetramethyl-benzofuran-6-yl)-3-hydroxycyclohex-2-en-1-one in 70 ml of absolute toluene was added 9.5 ml of anhydrous propionic acid and refluxed for 4 hours. The reaction mixture was cooled to room temperature and concentrated under reduced pressure to afford an oily residue. To the solution of residue in 70 ml of absolute toluene was added 0.67 g of 4-dimethylaminopyridine, refluxed for 15 hours and cooled to room temperature and then concentrated under reduced pressure to afford a crude product. Final purification was carried by silica-gel column chromatography to afford 3.25 g of 5-(7-chloro-2,3-dihydro-2,3,4,5-tetramethylbenzofuran-6-yl)-2-propionyl-3-hydroxycyclohex-2-en-1-one as a yellow solid.

¹H NMR (CDCl₃): δ1.1 (t, 3H), 1.5 (s, 6H), 2.1 (s, 3H), 2.3 (s, 3H), 2.4–2.6 (m, 2H), 2.9–3.3 (m, 6H), 3.5–4.0 (m, 1H), 13.5 (br, 1H).

vii) 5-(7-Chloro-2,3-dihydro-2,2,4,5-tetramethylbenzofuran-6-yl)-2-[1-ethoxy-imino)propyl]-3-hydroxycyclohex-2-en-1-one.

To a solution of 0.4 g of the 5-(7-chloro-2,3-dihydro-2, 3,4,5-tetramethyl-benzofuran-6-yl)-2-propionyl-3-hydroxycyclohex-2-en-1-one in 10 ml of ethanol was added 0.176 g of sodium acetate and 0.114 g of ethoxyamine hydrochloride. After stirring at room temperature for 24 hours, the reaction mixture was quenched with 50 ml of water and extracted with diethyl ether. The combined organic extracts were dried over anhydrous magnesium sulfate, filtered and concentrated under the reduced pressure to afford 0.38 g of 5-(7-chloro-2,3-dihydro-2,2,4,5-tetramethylbenzofuran-6 -yl)-2-[1-ethoxyimino)propyl]-3-hydroxycyclohex-2-en-1-one.

¹H NMR (CDCl₃): δ1.1 (m, 6H), 1.4 (s, 6H), 2.1 (s, 3H), 2.2 (s, 3H), 2.3–2.6 (m, 2H), 2.8–3.2 (m, 6H), 3.5–3.8 (m, 1H), 4.0 (q, 2H), 13.2 (br, 1H).

EXAMPLE 3

5-(2,3-Dihydro-2,2,4,5,6-pentamethylbenzofuran-7-yl)-2-[1-(ethoxyimino) butyryl]-3-hydroxycyclohex-2-en-1-one (58)

i) Methallyl 3,4,5-trimethylphenyl ether.

To a solution 20 g of 3,4,5-trimethylphenol in 150 ml of absolute acetone was added 22 ml of 3-chloro-2-methylpropene and 20.3 g of anhydrous potassium carbonate. After refluxing for 45 hours, the reaction mixture was filtered, washed with acetone, concentrated under reduced pressure and diluted with 200 ml of diethyl ether. The mixture was extracted three times with 50 ml of 2N hydrochloric acid and 50 ml of 20% aqueous solution of sodium hydroxide. The organic extract was dried over anhydrous magnesium sulfate, filtered and concentrated under the reduced pressure to afford a crude product. Final purification was carried by silica-gel column chromatography to afford 27 g of methallyl 3,4,5-trimethylphenyl ether as yellow oil.

¹H NMR (CDCl₃): δ1.8 (s, 3H), 2.05 (s, 3H), 2.2 (s, 6H), 4.4 (s, 2H), 5.0–5.1 (d, 2H), 6.85 (s, 2H).

ii) 2,3-Dihydro-2,2,4,5,6-pentamethylbenzofuran.

To a solution of 27 g of the methallyl 3,4,5-trimethylphenyl ether in 200 ml absolute dichloromethane at −70° C. was added 18.5 g of AlCl₃ under a current of nitrogen gas. After stirring and warming to room temperature over a period of 1 hour, the reaction mixture was added 300 ml of ice-water and stirred for 30 minutes. Thereafter the aqueous layer was extracted with dichloromethane. The combined organic extracts were washed with water, dried over anhydrous magnesium sulfate and concentrated under reduced pressure to afford a crude product. Final purification was carried by silica-gel column chromatography to afford 22 g of 2,3-dihydro-2,2,4,5,6-pentamethylbenzofuran as yellow oil.

¹H NMR (CDCl₃): δ1.5 (s, 6H), 2.2 (s, 3H), 2.3 (s, 3H), 2.4 (s, 3H), 3.1 (s, 2H), 6.6 (s, 1H).

iii) 2,3-Dihydro-2,2,4,5,6-pentamethylbenzofuran-7-carboxaldehyde.

To a solution of 22 g of the 2,3-dihydro-2,2,4,5,6-pentamethylbenzofuran in 150 ml of absolute dichloromethane was added 12.8 ml of titanium chloride(IV) and 15.8 ml of a α,α-dichloromethyl methyl ether at 0° C. With stirring at room temperature for 1 hour, the reaction mixture was quenched with 300 ml of water and the aqueous layer was extracted with dichloromethane. The combined organic extracts were dried over anhydrous magnesium sulfate, filtered and concentrated under reduced pressure to afford 20 g of 2,3-dihydro-2,2,4,5,6-pentamethylbenzofuran-7-carboxaldehyde as a white solid.

m.p.: 87°–88° C.

¹H NMR (CDCl₃): δ1.5 (s, 6H), 2.2 (s, 3H), 2.3 (s, 3H), 2.4 (s, 3H), 3.1 (s, 2H), 6.6 (s, 1H).

iv) 4-(2,3-Dihydro-2,2,4,5,6-pentamethylbenzofuran-7-yl)-3-buten-2-one.

To a solution of 19.5 g of the 2,3-dihydro-2,2,4,5,6-pentamethylbenzofuran-7-carboxaldehyde in 65 ml of acetone was added 32 ml of water and 36 g of 1% aqueous solution of sodium hydroxide. After refluxing for 20 hours, the reaction mixture was quenched with 2N hydrochloric acid and the aqueous layer was extracted three times with 50 ml of diethyl ether. The combined organic extracts were dried over anhydrous magnesium sulfate, filtered and concentrated under reduced pressure to afford a crude product. Final purification was carried by recrystallization to afford 17.6 g of 4-(2,3-dihydro-2,2,4,5,6-pentamethylbenzofuran-7-yl)-3-buten-2-one as a yellow plate crystal.

m.p.: 125° C.

$^1$H NMR (CDCl$_3$): δ1.5 (s, 6H), 2.2 (s, 3H), 2.4 (s, 6H), 3.0 (s, 2H), 7.0–7.3 (d, 1H), 7.8–8.1 (d, 1H).

v) 5-(2,3-Dihydro-2,2,4,5,6-pentamethylbenzofuran-7-yl)cyclohexane-1,3-dione.

To a solution of 1.57 g of sodium in 68 ml of absolute methanol was added 10.35 ml of diethyl malonate. After stirring for 20 minutes, the mixture was added 8 g of the 4-(2,3-dihydro-2,2,4,5,6-pentamethylbenzofuran-7-yl)-3-buten-2-one in 17.5 g of absolute methanol, refluxed for 4 hours and added 150 g of 5% aqueous solution of sodium hydroxide. The reaction mixture was cooled to room temperature and washed three times with 50 ml of diethyl ether. 2N aqueous solution of hydrochloric acid was added dropwise into the aqueous layer until the bubble of carbon dioxide ceased. And then, solid was dissolved in ethyl acetate and washed with water. The combined organic layer was dried over anhydrous magnesium sulfate and concentrated under reduced pressure to afford 16.7 g of 5-(2,3-dihydro-2,2,4,5,6-pentamethyl-benzofuran-7-yl)cyclohexane-1,3-dione as a yellow solid.

$^1$H NMR (CDCl$_3$): δ1.5 (s, 3H), 2.2–2.3 (3s, 9H), 2.8–3.0 (m, 4H), 3.2–3.4 (m,1H), 3.5–3.7 (m, 2H), 5.5 (s, 1H), 8.3–8.6 (br, 1H).

vi) 2-Butyryl-5-(2,3-dihydro-2,3,4,5,6-pentamethylbenzofuran-7-yl)-3-hydroxycy-clohex-2-en-1-one.

To a solution of 8.3 g of the 5-(2,3-dihydro-2,2,4,5,6-pentamethylbenzofuran-7-yl)cyclohexane-1,3-dione in 80 ml of absolute toluene was added 18 ml of anhydrous butyric acid and refluxed for 4 hours. The reaction mixture was concentrated under reduced pressure to afford a residue. To the solution of the residue in 100 ml of toluene was added 1.6 g of dimethylaminopyridine. After refluxing for 15 hours, the reaction mixture was cooled to room temperature and concentrated under reduced pressure to afford a crude product. Final purification was carried by silica-gel column chromatography to afford 6.1 g of 2-butyryl-5-(2,3-dihydro-2,3,4,5,6-penta-methylbenzofuran- 7-yl)-3-hydroxycyclohex-2-en-1-one as a yellow solid.

m.p.: 119°–120° C.

$^1$H NMR (CDCl$_3$): δ1.0 (t,3H), 1.5 (s, 6H), 1.6–1.75 (q, 2H), 2.15 (s, 6H), 2.25 (s, 3H), 2.4–2.6 (m, 2H), 2.9–3.0 (m, 4H), 3.2–3.5 (m, 1H), 3.6–3.75 (m, 2H).

vii) 5-(2,3-Dihydro-2,2,4,5,6-pentamethylbenzofuran-7-yl)-2-[1-(ethoxyimino) butyryl]-3-hydroxycyclohex-2-en-1-one.

To a solution of the 2-butyryl-5-(2,3-dihydro-2,3,4,5,6-pentamethylbenzofuran-7-yl)-3-hydroxycyclohex-2-en-1-one in ethanol was added 88 mg of sodium acetate and 58 mg of ethoxyamine hydrochloride. After stirring at room temperature for 24 hours, the reaction mixture was quenched with 20 ml of water and extracted three times with 30 ml of diethyl ether. The combined organic extracts were dried over anhydrous magnesium sulfate, filtered and concentrated under the reduced pressure to afford a crude product. Final purification was carried by recrystallization to afford 0.19 g of 5-(2,3-dihydro-2,2,4,5,6-pentamethylbenzofuran-7-yl)-2-[1-(ethoxyimino)butyryl]-3-hydroxycyclohex-2-en-1-one as a white solid.

$^1$H NMR (CDCl$_3$): δ1.1 (t,3H), 1.4 (t, 3H), 1.5 (t, 3H), 1.6–1.75 (q, 2H), 2.2 (s, 6H), 2.3 (s, 3H), 2.4–2.6 (m, 2H), 2.9–3.1 (m, 4H), 3.3–3.5 (m, 1H), 3.6–3.7 (m, 2H), 4.1–4.3 (q, 2H), 13.5 (s, 1H).

EXAMPLE 4

5-(2,3-Dihydro-2,2,4,5,7-pentamethylbenzofuran-6-yl)-2-[1-(ethoxyimino)propyl]-3-hydroxycyclohex-2-en-1-one (73)

i) Methallyl 2,5-dimethylphenyl ether.

To a solution 122.2 g of 2,5-dimethylphenol in 300 ml of acetone was added 83 g of anhydrous potassium carbonate and 150 ml of 3-chloro-2-methylpropene. After refluxing for 65 hours, the reaction mixture was filtered and concentrated under reduced pressure and diluted with 200 ml diethyl ether. The mixture was washed three times with 100 ml of 10% aqueous solution of sodium hydroxide. The combined organic extracts were washed with water, dried over anhydrous magnesium sulfate, filtered and concentrated under the reduced pressure to afford 168 g of methallyl 2,5-dimethylphenyl ether as colorless oil.

b.p.: 70°–74° C./0.15 torr.

$^1$H NMR (CDCl$_3$): δ1.8 (s, 3H), 2.3 (2s, 6H), 4.4 (s, 2H), 5.0 (d, 2H), 6.7–7.1 (m, 3H).

ii) 2,3-Dihydro-2,2,4,7-tetramethylbenzofuran.

To a solution of 168 g of the methallyl 2,5-dimethylphenyl ether in 500 ml of absolute dichloromethane at −70° C. was added 64 g of AlCl$_3$ under a current of nitrogen gas. After stirring and warming to room temperature over a period of 1 hour, the reaction mixture was added 1 l of water and stirred for 30 minutes, and the aqueous layer was extracted with dichloromethane. The organic extract was washed with water, dried over anhydrous magnesium sulfate and concentrated under reduced pressure to afford a crude product. Final purification was carried by vacuum distillation to afford 110 g of 2,3-dihydro-2,2,4,7-tetramethylbenzofuran as colorless oil.

b.p.: 58°–62° C./0.15 torr.

$^1$H NMR (CDCl$_3$): δ1.5 (s, 6H), 2.15 (2s, 6H), 2.95 (s, 2H), 6.5–7.0 (m, 2H).

iii) 2,3-Dihydro-2,2,4,7-tetramethylbenzofuran-5-carboxaldehyde.

To a solution of 110 g of the 2,3-dihydro-2,2,4,7-tetramethylbenzofuran in 500 ml of absolute dichloromethane was added 68.5 ml of titanium chloride(IV) and 56.5 ml of α,α-dichloromethyl methyl ether at 0° C. With stirring at room temperature for 45 minutes and refluxing for 15 minutes, the reaction mixture was quenched with 1 l of water and the aqueous layer was extracted with dichloromethane. The combined organic extracts were dried over anhydrous magnesium sulfate, filtered and concentrated under reduced pressure to afford a crude product. Final purification was carried by recrystallization to afford 104 g of 2,3-dihydro -2,2,4,7-tetramethyl-benzofuran-5-carboxaldehyde as a white solid.

m.p.: 103° C.

$^1$H NMR (CDCl$_3$): δ1.5 (s, 6H), 2.2 (s, 3H), 2.5 (s, 3H), 3.0 (s, 2H), 7.45 (s, 1H), 10.05 (s, 1H).

iv) 2,3-Dihydro-2,2,4,5,7-pentamethylbenzofuran.

To a suspension of 9.75 g of lithium aluminum hydride in 200 ml of absolute diethyl ether was added 34.27 g of AlCl$_3$ and added dropwise a mixture of 42 g of the 2,3-dihydro-2,2,4,7-tetramethylbenzofuran-5-carboxaldehyde and 27.4 g of AlCl₃ in 100 ml of absolute diethyl ether. After stirring for 30 minutes, the reaction mixture was quenched with 10 ml of ethyl acetate and added with 100 ml of water and 100 ml of 2N aqueous solution of hydrochloric acid. The organic extract was dried over anhydrous magnesium sulfate, filtered and concentrated under reduced pressure to afford a crude product. Final purification was carried by vacuum distillation to afford 34.5 g of 2,3-dihydro-2,2,4,5,7-pentamethylbenzofuran as colorless oil.

b.p.: 78°–81° C./0.15 torr.

¹H NMR (CDCl₃): δ1.45 (s, 6H), 2.15 (3s, 9H), 2.95 (s, 2H), 6.8 (s, 1H).

v) 2,3-Dihydro-2,2,4,5,7-pentamethylbenzofuran-6-carboxaldehyde.

To a solution of 34.5 g of the 2,3-dihydro-2,2,4,5,7-pentamethylbenzofuran in 200 ml of absolute dichloromethane was added 200 ml of titanium chloride (IV) and 18 ml of α,α-dichloromethyl methyl ether at 0° C. With stirring at room temperature for 45 minutes and refluxing for 15 minutes, the reaction mixture was quenched with 300 ml of water and the aqueous layer was extracted with dichloromethane. The combined organic extracts were dried over anhydrous magnesium sulfate, filtered and concentrated under reduced pressure to afford a crude product. Final purification was carried by recrystallization to afford 37.2 g of 2,3-dihydro-2,2,4,5,7-pentamethyl-benzofuran-6-carboxaldehyde as a white solid.

m.p.: 93° C.

¹H NMR (CDCl₃): δ1.5 (s, 6H), 2.2 (s, 3H), 2.4 (2s, 6H), 3.0 (s, 2H), 10.6 (s, 1H)

vi) 4-(2,3-Dihydro-2,2,4,5,7-pentamethylbenzofuran-6-yl)-3-butene-2-one.

To a solution of 37 g of the 2,3-dihydro-2,2,4,5,7-pentamethylbenzofuran-6-carboxaldehyde in 125 ml of acetone was added 60 ml of water and 68 g of 2% aqueous solution of sodium hydroxide. After refluxing for 20 hours, the reaction mixture was quenched with 10 ml of 2N aqueous solution of hydrochloric acid and the aqueous layer was extracted with dichloromethane. The combined organic extracts were dried over anhydrous magnesium sulfate, filtered and concentrated under reduced pressure to afford a crude product. Final purification was carried by recrystallization to afford 42.4 g of 4-(2,3-dihydro-2,2,4,5,7-pentamethylbenzofuran-6-yl)-3-butene-2-one.

¹H NMR (CDCl₃): δ1.5 (s, 6H), 2.15 (3s, 9H), 2.4 (s, 3H), 3.0 (s, 2H), 6.4–6.7 (2s, 1H), 7.3–7.5 (2s, 1H).

vii) 5-(2,3-Dihydro-2,2,4,5,7-pentamethylbenzofuran-6-yl)-3-hydroxycyclohex-2-en-1-one.

To a solution of 3.8 g of sodium 140 ml of absolute methanol was added 25 ml of diethyl malonate. After stirring for 20 minutes, the mixture was added 42.4 g of the 4-(2,3-dihydro-2,2,4,5,7-pentamethylbenzofuran-6-yl)-3-butene-2-one in 140 ml of absolute methanol, refluxed for 4 hours and 200 ml of 10% aqueous solution of sodium hydroxide. The reaction mixture was cooled to room temperature and washed with diethyl ether. 2N aqueous solution of hydrochloric acid was added dropwise into the aqueous layer until the bubble ceased. And then, solid was dissolved in ethyl acetate and washed with water. The combined organic layer was dried over anhydrous magnesium sulfate and concentrated under reduced pressure to afford 38.8 g of 5-(2,3-dihydro-2,2,4,5,7-pentamethylbenzofuran-6-yl)-3-hydroxycyclohex-2-en-1-one.

m.p.: 121°–123° C.

¹H NMR (CDCl₃): δ1.5 (s, 6H), 2.1 (s, 3H), 2.2 (s, 6H), 2.4–3.5 (m, 7H), 5.3 (s, 1H).

viii) 5-(2,3-Dihydro-2,2,4,5,7-pentamethylbenzofuran-6-yl)- 2-propionyl-3-hydroxycyclohex-2-en-1-one.

To a solution of 12 g of the 5-(2,3-dihydro-2,2,4,5,7-pentamethylbenzofuran-6-yl)-3-hydroxycyclohex-2-en-1-one in 100 ml of absolute toluene was added 20.5 ml of anhydrous propionic acid and refluxed for 4 hours. The reaction mixture was cooled to room temperature and concentrated under reduced pressure to afford a residue. To a solution of the residue in 100 ml of absolute toluene was added 0.98 g of dimethylaminopyridine, After refluxing 20 hours, the reaction mixture was cooled to room temperature and concentrated under reduced pressure to afford a crude product. Final purification was carried by silica-gel column chromatography to afford 3.9 g of 5-(2,3-dihydro-2,2,4,5,7-pentamethylbenzofuran-6-yl)-2-propionyl-3-hydroxycyclohex-2-en-1-one as a yellow solid.

m.p.: 74–76° C.

¹H NMR (CDCl₃): δ1.1 (t, 3H), 1.4 (s, 6H), 2.1–2.3 (3s, 9H), 2.5–3.7 (m, 9H).

ix) 5-(2,3-Dihydro-2,2,4,5,7-pentamethylbenzofuran-6-yl)-2-[1-(ethoxyimino) propyl]-3-hydroxycyclohex-2-en-1-one.

To a solution 0.3 g of the 5-(2,3-dihydro-2,2,4,5,7-pentamethylbenzofuran-6-yl)-2-propionyl-3-hydroxycyclohex-2-en-1-one in 10 ml of ethanol was added 0.14 g of sodium acetate and 0.09 g of ethoxyamine hydrochloric acid. After stirring at room temperature for 20 hours, the reaction mixture was quenched with 20 ml water and extracted with diethyl ether. The combined organic extracts were dried over anhydrous magnesium sulfate, filtered and concentrated under the reduced pressure to afford a crude product. Final purification was carried by silica-gel column chromatography to afford 0.28 g of 5-(2,3-dihydro-2,2,4,5, 7-pentamethylbenzofuran- 6-yl)-2-[1-(ethoxyimino)propyl]-3-hydroxycyclohex-2-en-1-one as yellow oil.

¹H NMR (CDCl₃): δ1.2 (t, 3H), 1.35 (t, 3H), 1.48 (s, 6H), 2.15 (s, 3H), 2.25 (s, 6H), 2.45–2.7 (m, 2H), 2.9–3.05 (m, 4H), 3.1–3.4 (m, 2H), 3.9–4.0 (m, 1H), 4.05–4.2 (q, 2H), 13.9 (br, 1H).

The compounds of formula(I) of the present invention are sufficiently tolerant on most broadleaf and grass crops such as soybeans, cotton, rice and wheat are may be useful for post-emergent control of grassy weeds in said crops.

The compounds of the present invention may be applied for instance in form of wettable powders, dust, flowable concentrates, granules, solutions or emulsifiable concentrates.

To prepare the above formulations can be used either solid carrier or liquid carrier. As solid carders, inorganic powders such as kaolinite, bentonite, montmorillonite, talc diatomaceous earth, mica, gypsum, calcium carbonate, apatite, synthesized silicon hydroxide hydrate; plant powders such as soy powder, wheat powder, sawdust, tabacco powder, starch powder, crystallized cellulose; polymers such as petroleum resin, vinyl chloride resin, ketone resin; alumina or beeswax etc. can be used.

And as liquid carriers, alcohols such as methanol, ethanol, ethyleneglycol, benzyl alcohol; aromatic hydrocarbons such as toluene, benzene, xylene, methyl naphthalene, halo hydrocarbons such as chloroform, carbon tetrachloride, chlorobenzene; ethers such as dioxane, tetrahydrofuran; ketones such as acetone, methyl ethyl ketone, cyclohexanone; esters such as ethyl acetate, butyl acetate, ethyleneglycol acetate; amides such as dimethyl formamide; nitriles such as acetonitrile; ether alcohols such as ethylene glycol, diethyl ethers or water etc. can be used.

Surfactants can be advantageously employed herein such as various cationic, anionic and nonionic surfactants.

Cationic surfactants include long chain alkylammonium salts such as cetyltrimethylammonium bromide, etc.

Anionic surfactants include alkali metal, alkaline earth metal and ammonium salts of alkylaryl sulfonic acids such as dodecylbenzenesulfonic acid; alkyl sulfonic acids; alkyl sulfuric acids such as laurylsulfuric acid; ligninsulfonic acid; arylsulfonic acids such as naphthalene sulfonic acid or dibutylnaphthalenesulfonic acid; lauryl ether sulfate; fatty alcohol sulfates; fatty acids; salts of sulfated hexadecanols, heptadecanols or octadecanols; salts of sulfated fatty alcohol glycol ethers, etc.

Examples of nonionic surfactants include condensation products of fatty alcohols such as oleyl alcohol or cetyl alcohol; phenols; alkylphenols or caster oil with ethylene oxide or propylene oxide; condensation products of naphthalene or naphthalene sulfonic acids with phenol or formaldehyde, etc.

The content of the compound represented by the above formula(I), while varying depending on the formulations, is usually from 1 to 50% by weight for the wattable powders, the granules or the emulsifiable formulations, and from 20 to 40% by weight for the flowable or the dry flowable formulations.

The application amount of compound represented by the formula(I) is from 60 g to 1000 g/ha, preferably from 60 g to 600 g/ha.

The active herbicidal compounds of this invention may be formulated with insecticides, fungicides, nematocides, plant growth regulators, fertilizers, other herbicides or other agricultural chemicals.

TEST: Herbicidal Activity Evaluation

The herbicidal activity test is proceeded according to the following methods.

The sterilized sandy loam soil is filled in test pot having a surface acre of 348 cm$^2$ for upland test conditions or 115 cm$^2$ for paddy test species were planted in furrows.

The pots for the pre-emergente tests were sprayed the soil one day after planting with test compound in a mixture of acetone and water containing up to 0.5% Tween 20.

The concentration of the test compound in solution was varied to give a range of application rates, generally 2.0 kg/ha and submultiples thereof. The pots were placed in a greenhouse and watered regularly at the soil surface for 21 days and herbicidal effects were visually rated by a percent control.

The pots for the post-emergent tests were placed in a greenhouse and watered for 9–14 days, then the foliage of test plants was sprayed with a solution of the test compound in a mixture of acetone and water containing a small amount of Tween 20.

After spraying the plants were kept for one day, then watered regularly for 14 to 21 days, and herbicidal activity data were recorded.

The herbicidal activity data were taken visually by percent control, wherein 0 signifies no herbicidal effect and 100 signifies complete kill.

Herbicidal activity data are shown in Table 5 for the compounds of the above formula(I)

The plant species employed in these tests were selected from the following:

| Common Name | Abbreviate Name | Scientific Name |
| --- | --- | --- |
| Corn | ZEAMX | Zea mays |
| Soybean | GLXMX | Glycine max |
| Cotton | GOSHI | Gossypium hispitum |
| Wheat | TRZAW | Triticum aestivum |
| Rice | ORYSA | Oryza sativa |
| Common sorgum | SORBI | Sorgum bicolor |
| Barnyardgrass | ECHOR | Echinochloa crus-galli |
| Japanese brome | BROJA | Bromus japonicus |
| Large crabgrass | DIGSA | Digitaria sanguinalis |
| Fall panicum | PANDI | Pandicum dichotomiflorum |
| Blacknight shade | SOLNI | Solanum nigrum |
| Indian jointvetch | AESIN | Aeschynomene indica |
| Velvetleaf | ABUTH | Abutilon avicennae |
| Cockebur | XANSI | Xanthium strumarium |
| Bindweed | CAGHE | Calystegia japonica |
| Green foxtail | SETVI | Setaria viridis |
| Orchard grass | DACGL | Dactylis glomerta |

The compounds of formula (I) of the present invention are used as herbicides or plant growth regulants, for example, the above compounds are suitable for selective elimination of weeds when useful plant is cultivated. Also, the compounds of formula (I) have the effect of growth inhibition and growth regulation for useful plant, for example, cereals, soybean, wheat or rice.

The compounds of formula (I) as prominent herbicides, may be applied directly to soil for pre-emergence treatment and to the plant for post-emergence treatment. The compounds of formula (I) of the present invention generally have more prominent herbicidal activity when are treated to leaves for post-emergence, and have strong safety for the broad-leaved plant, for example, soybean, cotton. And these compounds have selectively herbicidal activity against grasses, and may be useful as herbicides in broad-leaved crops.

Certain of formula (I) compounds of the present invention especially have prominent selectivity within the group of grasses and may be used at rate sufficient to control grass weeds in cultivated crops, for example, rice, wheat or barley, and have selectively herbicidal activity against wild grasses such as wildoat or barnyardgrass.

TABLE 5

| Compound No. | Application method | kg/ha | ZEAMX | GLXMX | GOSHI | TRZAW | ORYSA | SORBI | ECHOR | BROJA | DIGSA | PANDI | SOLNI | AESIN | ABUTH | XANSI | CAGHE |
|---|---|---|---|---|---|---|---|---|---|---|---|---|---|---|---|---|---|
| 1 | PRE | 2 | 100 | 10 | 20 | 100 | 100 | 100 | 100 | 100 | 100 | 100 | — | 0 | 0 | 100 | 20 |
|   |     | 0.5 | 90 | 0 | 0 | 90 | 100 | 100 | 100 | 100 | 100 | 100 | — | 0 | 0 | 0 | 0 |
|   |     | 0.125 | 0 | 0 | 0 | 0 | 10 | 0 | 0 | 50 | 40 | 100 | — | 0 | 0 | 0 | 0 |
|   |     | 0.03 | 0 | 0 | 0 | 0 | 0 | 0 | 0 | 0 | 0 | 100 | 0 | 0 | 0 | 0 | 0 |
|   | POST | 2 | 100 | 50 | 100 | 100 | 100 | 100 | 100 | 100 | 100 | 100 | 0 | 0 | 0 | 0 | 0 |
|   |      | 0.5 | 100 | 0 | 0 | 90 | 100 | 100 | 100 | 100 | 100 | 100 | 0 | 0 | 0 | 0 | 0 |
|   |      | 0.125 | 90 | 0 | 0 | 60 | 90 | 100 | 90 | 65 | 100 | 100 | 0 | 0 | 0 | 0 | 0 |
|   |      | 0.03 | 40 | 0 | 0 | 0 | 0 | 50 | 0 | 0 | 50 | 50 | 0 | 0 | 0 | 0 | 0 |
| 2 | PRE | 2 | 30 | 0 | 0 | 0 | 40 | 65 | 100 | 100 | 100 | 100 | — | 0 | 0 | 0 | 0 |
|   |     | 0.5 | 0 | 20 | 30 | 0 | 40 | 20 | 80 | 80 | 100 | 100 | — | 0 | 0 | 0 | 30 |
|   |     | 0.125 | 0 | 0 | 0 | 0 | 20 | 0 | 0 | 40 | 50 | 50 | — | 0 | 0 | 0 | 10 |
|   |     | 0.03 | 0 | 0 | 0 | 0 | 0 | 0 | 0 | 0 | 0 | 0 | 0 | 0 | 0 | 0 | 0 |
|   | POST | 2 | 90 | 0 | 0 | 0 | 80 | 40 | 100 | 100 | 100 | 100 | — | 0 | 0 | 0 | 40 |
|   |      | 0.5 | 80 | 0 | 0 | 0 | 60 | 30 | 100 | 100 | 100 | 100 | — | 0 | 0 | 0 | 0 |
|   |      | 0.125 | 60 | 0 | 0 | 0 | 30 | 0 | 60 | 40 | 70 | 90 | — | 0 | 0 | 0 | 0 |
|   |      | 0.03 | 0 | 0 | 0 | 0 | 0 | 0 | 0 | 0 | 0 | 0 | 0 | 0 | 0 | 0 | 0 |
| 3 | PRE | 2 | 40 | 10 | 20 | 80 | 70 | 100 | 100 | 100 | 100 | 100 | 0 | 0 | 0 | 20 | 30 |
|   |     | 0.5 | 60 | 0 | 0 | 50 | 80 | 100 | 100 | 100 | 100 | 60 | 0 | 0 | 0 | 10 | 10 |
|   |     | 0.125 | 20 | 0 | 0 | 20 | 40 | 50 | 50 | 20 | 40 | 100 | 0 | 0 | 0 | 0 | 0 |
|   |     | 0.03 | 0 | 0 | 0 | 0 | 0 | 0 | 30 | 0 | 0 | 60 | 0 | 0 | 0 | 0 | 0 |
|   | POST | 2 | 90 | 0 | 40 | 100 | 100 | 100 | 100 | 100 | 100 | 100 | 0 | 0 | 0 | 0 | 0 |
|   |      | 0.5 | 90 | 0 | 0 | 60 | 90 | 40 | 100 | 100 | 100 | 90 | 0 | 0 | 0 | 0 | 0 |
|   |      | 0.125 | 30 | 0 | 0 | 0 | 60 | 0 | 90 | 90 | 40 | 60 | 0 | 0 | 0 | 0 | 0 |
|   |      | 0.03 | 20 | 0 | 0 | 0 | 30 | 0 | 0 | 0 | 0 | 0 | 0 | 0 | 0 | 0 | 0 |
| 4 | PRE | 2 | 0 | 0 | 0 | 0 | 0 | 40 | 100 | 100 | 100 | 100 | 0 | 0 | 0 | 100 | 30 |
|   |     | 0.5 | 0 | 0 | 0 | 0 | 0 | 30 | 100 | 100 | 100 | 100 | 0 | 0 | 0 | 20 | 10 |
|   |     | 0.125 | 0 | 0 | 0 | 0 | 0 | 10 | 20 | 60 | 40 | 50 | 0 | 0 | 0 | 10 | 0 |
|   |     | 0.03 | 0 | 0 | 0 | 0 | 0 | 0 | 0 | 0 | 0 | 0 | 0 | 0 | 0 | 0 | 0 |
|   | POST | 2 | 100 | 0 | 20 | 60 | 90 | 0 | 100 | 100 | 100 | 100 | 0 | 0 | 0 | 0 | 0 |
|   |      | 0.5 | 90 | 0 | 0 | 40 | 80 | 0 | 100 | 60 | 100 | 100 | 0 | 0 | 0 | 0 | 0 |
|   |      | 0.125 | 40 | 0 | 0 | 0 | 40 | 0 | 40 | 0 | 80 | 50 | 0 | 0 | 0 | 0 | 0 |
|   |      | 0.03 | 0 | 0 | 0 | 0 | 10 | 0 | 0 | 0 | 20 | 30 | 0 | 0 | 0 | 0 | 0 |
| 5 | PRE | 2 | 0 | 0 | 40 | 0 | 0 | 40 | 100 | 100 | 100 | 100 | 0 | 0 | 0 | 100 | 0 |
|   |     | 0.5 | 0 | 0 | 0 | 0 | 0 | 30 | 100 | 60 | 100 | 100 | 0 | 0 | 0 | 20 | 0 |
|   |     | 0.125 | 0 | 0 | 0 | 0 | 0 | 0 | 20 | 20 | 80 | 60 | 0 | 0 | 0 | 10 | 0 |
|   |     | 0.06 | 0 | 0 | 0 | 0 | 0 | 0 | 0 | 0 | 40 | 0 | 0 | 0 | 0 | 0 | 0 |
|   | POST | 2 | 50 | 0 | 0 | 0 | 40 | 0 | 100 | 60 | 100 | 100 | 100 | 0 | 0 | 100 | 0 |
|   |      | 0.5 | 50 | 0 | 0 | 0 | 20 | 0 | 100 | 20 | 60 | 70 | 60 | 0 | 0 | 0 | 0 |
|   |      | 0.125 | 0 | 0 | 0 | 0 | 0 | 0 | 80 | 0 | 0 | 30 | 0 | 0 | 0 | 0 | 0 |
|   |      | 0.03 | 0 | 0 | 0 | 0 | 0 | 0 | 0 | 0 | 0 | 0 | 0 | 0 | 0 | 0 | 0 |
| 10 | PRE | 2 | 0 | 0 | 0 | 0 | 0 | 80 | 80 | 100 | 100 | 100 | — | 0 | 0 | 70 | 30 |
|    |     | 0.5 | 0 | 0 | 0 | 0 | 0 | 60 | 70 | 80 | 100 | 100 | — | 0 | 0 | 30 | 0 |
|    |     | 0.125 | 0 | 0 | 0 | 0 | 0 | 0 | 40 | 60 | 60 | 90 | — | 0 | 0 | 0 | 0 |
|    |     | 0.03 | 0 | 20 | 0 | 0 | 0 | 0 | 0 | 0 | 20 | 0 | — | 0 | 0 | 0 | 0 |
|    | POST | 2 | 50 | 20 | 0 | 0 | 30 | 30 | 100 | 100 | 100 | 100 | 30 | 0 | 0 | 0 | 100 |

TABLE 5-continued

Herbicidal Activity

| Compound No. | Application method | kg/ha | ZEAMX | GLXMX | GOSHI | TRZAW | ORYSA | SORBI | ECHOR | BROJA | DIGSA | PANDI | SOLNI | AESIN | ABUTH | XANSI | CAGHE |
|---|---|---|---|---|---|---|---|---|---|---|---|---|---|---|---|---|---|
| 12 | PRE | 0.5 | 40 | 0 | 0 | 0 | 20 | 0 | 100 | 100 | 100 | 100 | 0 | 0 | 0 | 0 | 60 |
|  |  | 0.125 | 0 | 0 | 0 | 0 | 0 | 0 | 100 | 60 | 100 | 100 | 0 | 0 | 0 | 0 | 0 |
|  |  | 0.03 | 0 | 0 | 0 | 0 | 0 | 20 | 60 | 0 | 0 | 70 | 0 | 0 | 0 | 0 | 0 |
|  | POST | 2 | 0 | 0 | 0 | 0 | 20 | 0 | 80 | 100 | 100 | 100 | — | 0 | 0 | 20 | 50 |
|  |  | 0.125 | 40 | 0 | 0 | 0 | 0 | 0 | 20 | 80 | 20 | 40 | — | 0 | 0 | 0 | 0 |
|  |  | 0.03 | 20 | 0 | 0 | 0 | 0 | 0 | 0 | 20 | 0 | 30 | — | 0 | 0 | 0 | 0 |
| 13 | PRE | 2 | 0 | 0 | 0 | 0 | 0 | 0 | 100 | 100 | 100 | 100 | 0 | 0 | 0 | 0 | 0 |
|  |  | 0.5 | 0 | 0 | 0 | 0 | 10 | 30 | 100 | 60 | 100 | 100 | 0 | 0 | 0 | 0 | 0 |
|  |  | 0.125 | 0 | 0 | 0 | 0 | 0 | 0 | 100 | 30 | 30 | 50 | 0 | 0 | 0 | 0 | 0 |
|  | POST | 2 | 0 | 0 | 0 | 0 | 0 | 0 | 40 | 80 | 100 | 100 | 0 | 0 | 0 | 0 | 0 |
|  |  | 0.5 | 0 | 0 | 0 | 0 | 0 | 0 | 80 | 40 | 20 | 20 | 0 | 0 | 0 | 0 | 0 |
|  |  | 0.125 | 0 | 0 | 0 | 0 | 0 | 0 | 0 | 0 | 0 | 0 | 0 | 0 | 0 | 0 | 0 |
| 15 | PRE | 2 | 0 | 0 | 0 | 0 | 0 | 100 | 60 | 100 | 100 | 100 | 0 | 0 | 0 | 0 | 0 |
|  |  | 0.5 | 0 | 0 | 0 | 0 | 0 | 0 | 60 | 30 | 70 | 50 | 0 | 0 | 0 | 0 | 0 |
|  |  | 0.125 | 0 | 0 | 0 | 0 | 0 | 0 | 0 | 0 | 0 | 0 | 0 | 0 | 0 | 0 | 0 |
|  | POST | 2 | 0 | 0 | 0 | 0 | 0 | 30 | 40 | 100 | 100 | 100 | 0 | 0 | 0 | 0 | 0 |
|  |  | 0.5 | 0 | 0 | 0 | 0 | 0 | 20 | 0 | 30 | 50 | 50 | 0 | 0 | 0 | 0 | 0 |
|  |  | 0.125 | 0 | 0 | 0 | 0 | 0 | 0 | 0 | 0 | 0 | 0 | 0 | 0 | 0 | 0 | 0 |
| 18 | PRE | 2 | 80 | 40 | 0 | 20 | 30 | 40 | 80 | 100 | 100 | 100 | 0 | 0 | 0 | 0 | 0 |
|  |  | 0.5 | 70 | 0 | 0 | 0 | 0 | 0 | 60 | 50 | 100 | 100 | 0 | 0 | 0 | 0 | 0 |
|  |  | 0.125 | 50 | 0 | 0 | 0 | 0 | 0 | 0 | 0 | 0 | 30 | 0 | 0 | 0 | 0 | 0 |
|  | POST | 1 | 20 | 0 | 0 | 20 | 30 | 100 | 100 | 100 | 100 | 100 | 0 | 0 | 0 | 0 | 0 |
|  |  | 0.25 | 0 | 0 | 0 | 30 | 0 | 20 | 20 | 70 | 100 | 0 | 0 | 0 | 0 | 0 | 0 |
|  |  | 0.0625 | 0 | 0 | 0 | 0 | 0 | 0 | 0 | 0 | 20 | 0 | 0 | 0 | 0 | 0 | 0 |
| 27 | PRE | 1 | 100 | 30 | 0 | 100 | 100 | 80 | 100 | 100 | 100 | 100 | 0 | 0 | 0 | 0 | 0 |
|  |  | 0.25 | 100 | 30 | 0 | 30 | 40 | 30 | 20 | 50 | 100 | 40 | 0 | 0 | 0 | 0 | 0 |
|  |  | 0.0625 | 0 | 10 | 0 | 0 | — | 0 | 0 | 40 | 0 | 0 | 0 | 0 | 0 | 0 | 0 |
|  | POST | 1 | 0 | 0 | 0 | 0 | 0 | 80 | 0 | 100 | 0 | 0 | 0 | 0 | 0 | 0 | 0 |
|  |  | 0.25 | 0 | 0 | 0 | 0 | 0 | 0 | 0 | 0 | 0 | 40 | 0 | 0 | 0 | 0 | 0 |
|  |  | 0.0156 | 0 | 0 | 0 | 0 | 0 | 0 | 0 | 0 | 0 | 0 | 0 | 0 | 0 | 0 | 0 |
| 28 | PRE | 2 | 40 | 0 | 0 | 0 | 100 | 100 | 100 | 100 | 100 | 100 | 40 | 65 | 40 | 20 | 40 |
|  |  | 0.5 | 0 | 0 | 0 | 100 | 40 | 100 | 100 | 100 | 100 | 100 | 0 | 0 | 0 | 0 | 0 |
|  |  | 0.125 | 0 | 0 | 0 | 100 | 100 | 70 | 100 | 65 | 60 | 65 | 0 | 0 | 0 | 0 | 0 |
|  | POST | 2 | 100 | 30 | 0 | 100 | 100 | 100 | 100 | 100 | 100 | 100 | 0 | 0 | 0 | 0 | 0 |
|  |  | 0.5 | 100 | 30 | 0 | 100 | 100 | 100 | 100 | 100 | 100 | 100 | 0 | 0 | 0 | 0 | 0 |
|  |  | 0.03125 | 100 | 10 | 0 | 60 | 100 | 50 | 100 | 100 | 100 | 100 | 0 | 0 | 0 | 0 | 0 |
|  | PRE | 2 | 100 | 0 | 0 | 0 | 20 | 80 | 100 | 100 | 100 | 100 | 0 | 0 | 0 | 0 | 0 |
|  |  | 0.5 | 20 | 0 | 0 | 0 | 0 | 80 | 100 | 100 | 100 | 100 | 0 | 0 | 0 | 0 | 0 |
|  |  | 0.125 | 0 | 0 | 0 | 0 | 0 | 60 | 40 | 100 | 100 | 100 | 0 | 0 | 0 | 0 | 0 |

TABLE 5-continued

Herbicidal Activity

| Compound No. | Application method | kg/ha | ZEAMX | GLXMX | GOSHI | TRZAW | ORYSA | SORBI | ECHOR | BROJA | DIGSA | PANDI | SOLNI | AESIN | ABUTH | XANSI | CAGHE |
|---|---|---|---|---|---|---|---|---|---|---|---|---|---|---|---|---|---|
| | POST | 0.03125 | 0 | 0 | 0 | 0 | 0 | 30 | 20 | 80 | 100 | 100 | 0 | 0 | 0 | 0 | 0 |
| 29 | | 2 | 100 | 0 | 0 | 100 | 100 | 100 | 100 | 100 | 100 | 100 | 0 | 0 | 0 | 0 | 0 |
| | PRE | 0.5 | 100 | 0 | 0 | 100 | 100 | 90 | 100 | 100 | 100 | 100 | 0 | 0 | 0 | 0 | 0 |
| | | 0.125 | 100 | 0 | 0 | 100 | 100 | 90 | 100 | 100 | 100 | 100 | 0 | 0 | 0 | 0 | 0 |
| | | 0.03125 | 100 | 0 | 30 | 60 | 90 | 65 | 100 | 100 | 100 | 100 | 0 | 0 | 0 | 0 | 0 |
| | POST | 2 | 0 | 0 | 0 | 0 | 30 | 40 | 100 | 100 | 100 | 100 | 0 | 0 | 0 | 0 | 0 |
| | | 0.5 | 0 | 0 | 0 | 0 | 0 | 20 | 30 | 50 | 50 | 100 | 0 | 0 | 0 | 0 | 0 |
| | | 0.125 | 0 | 0 | 0 | 0 | 0 | 0 | 0 | 0 | 0 | 80 | 0 | 0 | 0 | 0 | 0 |
| 30 | | 0.03125 | 100 | 0 | 0 | 70 | 100 | 80 | 100 | 100 | 100 | 100 | 0 | 0 | 30 | 0 | 100 |
| | PRE | 2 | 100 | 0 | 0 | 40 | 100 | 80 | 100 | 100 | 100 | 80 | 0 | 0 | 20 | 20 | 10 |
| | | 0.5 | 100 | 0 | 0 | 30 | 60 | 40 | 100 | 100 | 100 | 100 | 0 | 0 | 0 | 0 | 0 |
| | | 0.125 | 20 | 0 | 0 | 0 | 0 | 0 | 100 | 60 | 70 | 90 | 0 | 0 | 0 | 0 | 0 |
| | | 0.03125 | 0 | 0 | 0 | 0 | 0 | 0 | 80 | 30 | 40 | 100 | 0 | 0 | 0 | 0 | 0 |
| | POST | 2 | 80 | 0 | 30 | 80 | 100 | 60 | 100 | 100 | 100 | 100 | 0 | 0 | 0 | 0 | 0 |
| | | 0.5 | 50 | 0 | 0 | 70 | 100 | 50 | 100 | 100 | 100 | 100 | — | 0 | 0 | 0 | 0 |
| | | 0.125 | 50 | 0 | 0 | 60 | 65 | 30 | 100 | 100 | 100 | 90 | — | 0 | 0 | 0 | 0 |
| | | 0.03 | 40 | 0 | 0 | 30 | 50 | 0 | 80 | 20 | 80 | 40 | — | 0 | 0 | 0 | 0 |
| | | 0.007 | 0 | 0 | 0 | 0 | 0 | 0 | 40 | 0 | 40 | 40 | — | 0 | 0 | 0 | 0 |
| 31 | PRE | 2 | 0 | 0 | 0 | 0 | 0 | 0 | 80 | 100 | 100 | 100 | 0 | 0 | 0 | 0 | 0 |
| | | 0.5 | 0 | 0 | 0 | 20 | 0 | 0 | 20 | 70 | 50 | 50 | 0 | 0 | 0 | 0 | 0 |
| | | 0.125 | 0 | 0 | 0 | 0 | 0 | 0 | 0 | 0 | 20 | 30 | 0 | 0 | 0 | 0 | 0 |
| | | 0.03125 | 0 | 0 | 0 | 0 | 0 | 0 | 0 | 0 | 0 | 0 | 0 | 0 | 0 | 0 | 0 |
| | POST | 2 | 100 | 0 | 0 | 20 | 70 | 20 | 100 | 100 | 100 | 100 | 0 | 0 | 0 | 0 | 0 |
| | | 0.5 | 100 | 0 | 0 | 0 | 50 | 0 | 90 | 90 | 100 | 100 | 0 | 0 | 0 | 0 | 0 |
| | | 0.125 | 70 | 0 | 0 | 0 | 40 | 0 | 60 | 60 | 70 | 60 | 0 | 0 | 0 | 0 | 0 |
| | | 0.03125 | 40 | 0 | 0 | 0 | 0 | 0 | 30 | 0 | 30 | 0 | 0 | 0 | 0 | 0 | 0 |
| 32 | PRE | 2 | 30 | 0 | 0 | 0 | 0 | 40 | 40 | 20 | 40 | 40 | 0 | 0 | 0 | 0 | 0 |
| | | 0.5 | 0 | 0 | 0 | 0 | 0 | 0 | 0 | 0 | 0 | 100 | 0 | 0 | 0 | 0 | 0 |
| | | 0.125 | 0 | 0 | 0 | 0 | 0 | 0 | 0 | 0 | 0 | 0 | 0 | 0 | 0 | 0 | 0 |
| | | 0.03125 | 0 | 0 | 0 | 0 | 0 | 0 | 0 | 0 | 0 | 0 | 0 | 0 | 0 | 0 | 0 |
| | POST | 2 | 100 | 70 | 65 | 100 | 100 | 100 | 100 | 100 | 100 | 100 | 80 | 60 | 100 | 30 | 40 |
| | | 0.5 | 100 | 40 | 60 | 70 | 100 | 90 | 100 | 100 | 100 | 100 | 80 | 30 | 100 | 0 | 0 |
| | | 0.125 | 100 | 0 | 0 | 60 | 100 | 40 | 100 | 100 | 100 | 100 | 0 | 0 | 0 | 0 | 0 |
| | | 0.03125 | 100 | 0 | 0 | 20 | 90 | 0 | 90 | 100 | 100 | 100 | 0 | 0 | 0 | 0 | 0 |
| 37 | PRE | 2 | 60 | 0 | 0 | 0 | 0 | 0 | 90 | 100 | 100 | 100 | 0 | 0 | 0 | 0 | 0 |
| | | 0.5 | 0 | 0 | 0 | 0 | 0 | 0 | 0 | 0 | 30 | 100 | 0 | 0 | 0 | 0 | 0 |
| | | 0.125 | 0 | 0 | 0 | 0 | 0 | 30 | 100 | 100 | 100 | 100 | 0 | 0 | 0 | 0 | 0 |
| | | 0.03125 | 0 | 0 | 0 | 0 | 80 | 20 | 100 | 100 | 100 | 100 | 0 | 0 | 0 | 0 | 0 |
| | POST | 2 | 100 | 10 | 0 | 0 | 30 | 0 | 100 | 100 | 80 | 100 | 0 | 0 | 0 | 0 | 0 |
| | | 0.5 | 100 | 0 | 0 | 0 | 0 | 0 | 100 | 100 | 100 | 100 | 0 | 0 | 0 | 0 | 0 |
| | | 0.125 | 100 | 0 | 0 | 0 | 0 | 0 | 100 | 100 | 100 | 100 | 0 | 0 | 0 | 0 | 0 |
| | | 0.03125 | 70 | 0 | 0 | 0 | 0 | 0 | 80 | 100 | 100 | 100 | 0 | 0 | 0 | 0 | 0 |

TABLE 5-continued

Herbicidal Activity

| Compound No. | Application method | kg/ha | ZEAMX | GLXMX | GOSHI | TRZAW | ORYSA | SORBI | ECHOR | BROJA | DIGSA | PANDI | SOLNI | AESIN | ABUTH | XANSI | CAGHE |
|---|---|---|---|---|---|---|---|---|---|---|---|---|---|---|---|---|---|
| 38 | PRE | 2 | 0 | 0 | 0 | 0 | 0 | 30 | 30 | 80 | 100 | 100 | 0 | 0 | 0 | 0 | 0 |
|  |  | 0.5 | 0 | 0 | 0 | 0 | 0 | 0 | 30 | 90 | 100 | 100 | 0 | 0 | 0 | 0 | 0 |
|  |  | 0.125 | 0 | 0 | 0 | 0 | 0 | 0 | 0 | 70 | 70 | 100 | 0 | 0 | 0 | 0 | 0 |
|  |  | 0.03125 | 0 | 0 | 0 | 0 | 0 | 0 | 0 | 0 | 20 | 100 | 0 | 0 | 0 | 0 | 0 |
|  | POST | 2 | 100 | 0 | 0 | 0 | 10 | 40 | 100 | 100 | 100 | 100 | 0 | 0 | 0 | 0 | 0 |
|  |  | 0.5 | 100 | 0 | 0 | 0 | 0 | 0 | 100 | 100 | 100 | 100 | 0 | 0 | 0 | 0 | 0 |
|  |  | 0.125 | 90 | 0 | 0 | 0 | 0 | 0 | 90 | 100 | 100 | 100 | 0 | 0 | 0 | 0 | 0 |
|  |  | 0.03125 | 40 | 0 | 0 | 0 | 0 | 0 | 40 | 80 | 100 | 100 | 0 | 0 | 0 | 0 | 0 |
| 39 | PRE | 2 | 0 | 0 | 0 | 0 | 0 | 30 | 60 | 100 | 100 | 100 | 0 | 0 | 0 | 0 | 0 |
|  |  | 0.5 | 0 | 0 | 0 | 0 | 0 | 20 | 20 | 60 | 90 | 100 | 0 | 0 | 0 | 0 | 0 |
|  |  | 0.125 | 0 | 0 | 0 | 0 | 0 | 0 | 0 | 30 | 90 | 100 | 20 | 0 | 0 | 0 | 0 |
|  |  | 0.03125 | 0 | 0 | 0 | 0 | 0 | 0 | 0 | 0 | 40 | 100 | 0 | 0 | 0 | 0 | 0 |
|  | POST | 2 | 80 | 0 | 0 | 0 | 40 | 0 | 100 | 100 | 100 | 100 | 0 | 0 | 0 | 0 | 0 |
|  |  | 0.5 | 90 | 0 | 0 | 0 | 20 | 0 | 80 | 100 | 90 | 100 | 0 | 0 | 0 | 0 | 0 |
|  |  | 0.125 | 40 | 0 | 0 | 0 | 0 | 0 | 50 | 50 | 40 | 100 | 0 | 0 | 0 | 0 | 0 |
|  |  | 0.03125 | 0 | 0 | 0 | 0 | 0 | 0 | 40 | 30 | 20 | 100 | 0 | 0 | 0 | 0 | 0 |
| 40 | PRE | 2 | 0 | 0 | 30 | 0 | 40 | 40 | 50 | 100 | 100 | 100 | 0 | 0 | 0 | 0 | 0 |
|  |  | 0.5 | 0 | 0 | 0 | 0 | 30 | 30 | 30 | 100 | 100 | 100 | 0 | 0 | 0 | 0 | 0 |
|  |  | 0.125 | 0 | 0 | 0 | 0 | 20 | 20 | 0 | 30 | 40 | 100 | 0 | 0 | 0 | 0 | 0 |
|  |  | 0.03125 | 0 | 0 | 0 | 0 | 0 | 0 | 0 | 30 | 40 | 100 | 0 | 0 | 0 | 0 | 0 |
|  | POST | 2 | 100 | 30 | 20 | 0 | 40 | 30 | 100 | 100 | 100 | 100 | 0 | 0 | 0 | 0 | 0 |
|  |  | 0.5 | 100 | 0 | 0 | 0 | 30 | 20 | 100 | 100 | 100 | 100 | 0 | 0 | 0 | 0 | 0 |
|  |  | 0.125 | 100 | 0 | 0 | 0 | 20 | 0 | 100 | 100 | 100 | 100 | 0 | 0 | 0 | 0 | 0 |
|  |  | 0.03125 | 30 | 0 | 0 | 0 | 0 | 0 | 40 | 60 | 100 | 60 | 0 | 0 | 0 | 0 | 0 |
| 43 | PRE | 1 | 30 | 40 | 0 | 0 | 0 | 100 | 100 | 40 | 100 | 20 | 20 | 0 | 0 | 0 | 0 |
|  |  | 0.25 | 0 | 0 | 0 | 0 | 0 | 100 | 0 | 0 | 0 | 0 | 0 | 0 | 0 | 0 | 0 |
|  |  | 0.0625 | 0 | 0 | 0 | 0 | 0 | 60 | 0 | 0 | 0 | 0 | 0 | 0 | 0 | 0 | 0 |
|  |  | 0.0156 | 0 | 0 | 0 | 0 | 0 | 0 | 0 | 0 | 0 | 0 | 0 | 0 | 0 | 0 | 0 |
|  | POST | 1 | 100 | 40 | 0 | 50 | 100 | 100 | 100 | 100 | 100 | 100 | 20 | 0 | 0 | 0 | 0 |
|  |  | 0.25 | 100 | 30 | 0 | 0 | 70 | 60 | 100 | 50 | 100 | 65 | 0 | 0 | 0 | 0 | 0 |
|  |  | 0.0625 | 100 | 30 | 0 | 0 | 50 | 0 | 100 | 0 | 100 | 30 | 0 | 0 | 0 | 0 | 0 |
|  |  | 0.0156 | 0 | 0 | 0 | 0 | 0 | 0 | 60 | 0 | 0 | 30 | 0 | 0 | 0 | 0 | 0 |

The unsubstituted compounds at the C-2 position of the formula (I) of the present invention are disclosed in U.S. Pat. No. 4,511,391.

For the purpose of comparison, herbicidal data for 2-[1-(ethoxyimino)butyl]-5-(2,3-dihydro-4,5,6-trimethylbenzo[b]furan-7-yl)-3-hydroxycyclohex-2-en-1-one (compound A) and 2-[1-(allyloxyimino)butyl]-5-(2,3-dihydro-4,5,6-trimethylbenzo[b]furan-7-yl)-3-hydroxycyclohex-2-en-1-one(compound B) are shown in Table 7.

Compared with herbicidal data for the corresponding C-2 dimethyl substituted analogs which are compound 9 and compound 11 of the compounds of the formula (I) of the present invention as shown in Table 6.

Compound 9 and compound 11 of formula (I) of the present invention have herbicidal properties superior to those of the corresponding unsubstituted compounds, compound A and compound B in both pre-emergent and post-emergent applications in side-by-side tests. Compound 9 and 11 also have markedly herbicidal activity against barnyardgrass and excellent safety to rice and wheat.

TABLE 6

Herbicidal Activity of Compound 9 and 11*

| Compound No. | Application method | kg/ha | Test Plant | | | | | | | | |
|---|---|---|---|---|---|---|---|---|---|---|---|
| | | | ZEAMX | GLXMX | GOSHI | TRZAW | ORYSA | SORBI | ECHOR | BROJA | DIGSA |
| 9 | PRE | 2 | 50 | 10 | 0 | 30 | 50 | 100 | 100 | 100 | 100 |
| | | 0.5 | 40 | 0 | 0 | 0 | 20 | 100 | 100 | 100 | 100 |
| | | 0.125 | 30 | 0 | 0 | 0 | 0 | 60 | 100 | 100 | 100 |
| | | 0.03 | 20 | 0 | 0 | 0 | 0 | 0 | 50 | 60 | 70 |
| | POST | 2 | 100 | 0 | 40 | 100 | 100 | 100 | 100 | 100 | 100 |
| | | 0.5 | 100 | 0 | 0 | 70 | 80 | 100 | 100 | 100 | 100 |
| | | 0.125 | 70 | 0 | 0 | 60 | 50 | 40 | 100 | 100 | 100 |
| | | 0.03 | 70 | 0 | 0 | 50 | 40 | 20 | 100 | 90 | 100 |
| 11 | PRE | 2 | 0 | 0 | 0 | 0 | 0 | 100 | 100 | 100 | 100 |
| | | 0.5 | 0 | 0 | 0 | 0 | 0 | 100 | 100 | 100 | 100 |
| | | 0.125 | 0 | 0 | 0 | 0 | 0 | 40 | 40 | 80 | 80 |
| | | 0.06 | 0 | 0 | 0 | 0 | 0 | 0 | 10 | 0 | 20 |
| | POST | 2 | 60 | 20 | 30 | 40 | 40 | 30 | 100 | 100 | 100 |
| | | 0.5 | 60 | 0 | 0 | 0 | 10 | 20 | 100 | 100 | 100 |
| | | 0.125 | 20 | 0 | 0 | 0 | 0 | 0 | 100 | 60 | 100 |
| | | 0.03 | 0 | 0 | 0 | 0 | 0 | 0 | 100 | 0 | 100 |

| Compound No. | Application method | kg/ha | Test Plant | | | | | |
|---|---|---|---|---|---|---|---|---|
| | | | PANDI | SOLNI | AESEN | ABUTH | XANSI | CAGHE |
| 9 | PRE | 2 | 100 | 0 | 0 | 0 | 100 | 30 |
| | | 0.5 | 100 | 0 | 0 | 0 | 0 | 0 |
| | | 0.125 | 100 | 0 | 0 | 0 | 0 | 0 |
| | | 0.03 | 100 | 0 | 0 | 0 | 0 | 0 |
| | POST | 2 | 100 | — | 0 | 0 | 0 | 0 |
| | | 0.5 | 100 | — | 0 | 0 | 0 | 0 |
| | | 0.125 | 100 | — | 0 | 0 | 0 | 0 |
| | | 0.03 | 90 | — | 0 | 0 | 0 | 0 |
| 11 | PRE | 2 | 100 | — | 0 | 0 | 0 | 0 |
| | | 0.5 | 100 | — | 0 | 0 | 0 | 0 |
| | | 0.125 | 70 | — | 0 | 0 | 0 | 0 |
| | | 0.06 | 0 | — | 0 | 0 | 0 | 0 |
| | POST | 2 | 100 | 0 | 0 | 0 | 0 | 0 |
| | | 0.5 | 100 | 0 | 0 | 0 | 0 | 0 |
| | | 0.125 | 100 | 0 | 0 | 0 | 0 | 0 |
| | | 0.03 | 100 | 0 | 0 | 0 | 0 | 0 |

*Compound 9 and 11 are compounds of formula (I) of the present invention

TABLE 7

Herbicidal Activity of Compound A and B*

| Compound No. | Application method | kg/ha | Test Plant | | | | | | |
|---|---|---|---|---|---|---|---|---|---|
| | | | ZEAMX | GLXMX | GOSHI | TRZAW | ORYSA | SORBI | ECHOR |
| A | PRE | 2 | 100 | 0 | 0 | 50 | 100 | 100 | 100 |
| | | 0.5 | 70 | 0 | 0 | 30 | 60 | 100 | 100 |
| | | 0.125 | 0 | 0 | 0 | 0 | 0 | 0 | 0 |
| | | 0.03 | 0 | 0 | 0 | 0 | 0 | 0 | 0 |
| | POST | 2 | 100 | 40 | 0 | 100 | 100 | 100 | 100 |
| | | 0.5 | 100 | 0 | 0 | 100 | 100 | 100 | 100 |
| | | 0.125 | 100 | 0 | 0 | 20 | 40 | 70 | 100 |
| | | 0.03 | 40 | 0 | 0 | 0 | 0 | 0 | 70 |
| B | PRE | 2 | 50 | 0 | 0 | 50 | 70 | 100 | 100 |
| | | 0.5 | 0 | 0 | 0 | 0 | 40 | 100 | 100 |

TABLE 7-continued

| | | | | | | | | |
|---|---|---|---|---|---|---|---|---|
| | | 0.125 | 0 | 0 | 0 | 0 | 0 | 0 | 30 |
| | | 0.03 | 0 | 0 | 0 | 0 | 0 | 0 | 0 |
| | POST | 2 | 100 | 0 | 0 | 100 | 100 | 100 | 100 |
| | | 0.5 | 100 | 0 | 0 | 50 | 100 | 70 | 100 |
| | | 0.125 | 40 | 0 | 0 | 0 | 40 | 0 | 100 |
| | | 0.03 | 20 | 0 | 0 | 0 | 0 | 0 | 0 |

| Compound No. | Application method | kg/ha | Test Plant |||||||
|---|---|---|---|---|---|---|---|---|---|
| | | | DIGSA | PANDI | SOLNI | AESIN | ABUTH | XANSI | CACHE |
| A | PRE | 2 | 100 | 100 | 100 | 0 | 0 | 0 | 0 |
| | | 0.5 | 80 | 100 | 100 | 0 | 0 | 0 | 0 |
| | | 0.125 | 0 | 40 | 80 | 0 | 0 | 0 | 0 |
| | | 0.03 | 0 | 0 | 0 | 0 | 0 | 0 | 0 |
| | POST | 2 | 100 | 100 | 0 | 30 | 0 | 0 | 0 |
| | | 0.5 | 100 | 100 | 0 | 0 | 0 | 0 | 0 |
| | | 0.125 | 0 | 80 | 0 | 0 | 0 | 0 | 0 |
| | | 0.03 | 30 | 0 | 0 | 0 | 0 | 0 | 0 |
| B | PRE | 2 | 100 | 100 | 0 | 0 | 0 | 0 | 0 |
| | | 0.5 | 100 | 100 | 0 | 0 | 0 | 0 | 0 |
| | | 0.125 | 40 | 20 | 0 | 0 | 0 | 0 | 0 |
| | | 0.03 | 0 | 0 | 0 | 0 | 0 | 0 | 0 |
| | POST | 2 | 100 | 100 | 0 | 30 | 0 | 0 | 0 |
| | | 0.5 | 100 | 100 | 0 | 0 | 0 | 0 | 0 |
| | | 0.125 | 100 | 0 | 0 | 0 | 0 | 0 | 0 |
| | | 0.03 | 20 | 0 | 0 | 0 | 0 | 0 | 0 |

*Compound A: 2-[1-(Ethoxyimino)butyl]-5-(2,3-dihydro-4,5,6-trimethylbenzo[b]furan-7-yl)-3-hydroxycyclohex-2-en-1-one.
Compound B: 2-[1-(Allyloxyimino)butyl]-5-(2,3-dihydro-4,5,6-trimethylbenzo[b]furan-7-yl)-3-hydroxycyclohex-2-en-1-one.

What is claimed is:

1. A compound of cyclohexane-1,3-dione derivatives of formula (I)

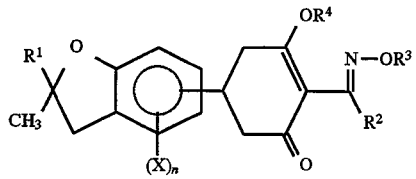

wherein,

X is selected from the group consisting of hydrogen, $C_1-C_6$ alkyl, $C_2-C_6$ alkoxy, halogen, $C_1-C_6$ haloalkyl, nitro, cyano, $C_1-C_6$ alkylthio, $C_1-C_6$ alkylsulfinyl, $C_1-C_6$ alkylsulfonyl, sulfamoyl, N-($C_1-C_6$ alkyl) sulfamoyl and N,N-di($C_1-C_6$ alkyl) sulfamoyl group;

(X)n represents number of X substituents on which may be the same or different benzene ring, where n is 1, 2 or 3, also, cyclohexyl moiety, one of the substituents on benzofuran ring, is possible substituted to 4, 5, 6 or 7 position, the (X)n can't be filled only with hydrogens and the (X)n can substitute position where cyclohexyl moiety is not substituted;

$R^1$ is selected from hydrogen and $C_1-C_4$ alkyl group;

$R^2$ is selected from $C_1-C_6$ alkyl, $C_2-C_6$ alkenyl and $C_2-C_6$ alkynyl group;

$R^3$ is selected from hydrogen, $C_1-C_6$ alkyl, $C_1-C_6$ haloalkyl, $C_2-C_6$ alkenyl, $C_2-C_6$ haloalkenyl, $C_2-C_6$ alkoxyalkyl, $C_2-C_6$ alkylthioalkyl, benzyl and $C_2-C_6$ haloalkanoyl group;

$R^4$ is selected from hydrogen, alkali metal cation, alkaline earth metal cation, $C_1-C_4$ alkanoyl, $C_1-C_4$ haloalkanoyl and benzoyl group.

2. The compound of cyclohexane-1,3-dione derivatives according to the claim 1, wherein X is selected from the group consisting of hydrogen, $C_1-C_6$ alkyl group and halogen wherein the (X)n can't be filled only with hydrogen and n is 1, 2 or 3; $R^1$ is selected from the group consisting of hydrogen and $C_1-C_6$ alkyl group; $R^2$ is selected from the group consisting of $C_1-C_6$ alkyl group; $R^3$ is selected from the group consisting of hydrogen, $C_1-C_6$ alkyl, $C_2-C_6$ alkenyl and $C_2-C_6$ haloalkenyl group; $R^4$ is hydrogen.

3. The compound of cyclohexane-1,3-dione derivatives according to the claim 1 to 2, wherein X is methyl group and n is 3; $R^1$ is selected from the group consisting of methyl and ethyl; $R^2$ is selected from the group of ethyl and propyl; $R^3$ is selected from the group of methyl, ethyl, allyl, crotyl, 2-chloroallyl, 3-chloroallyl; $R^4$ is hydrogen.

4. The compound according to the claim 1 of formula (I-a)

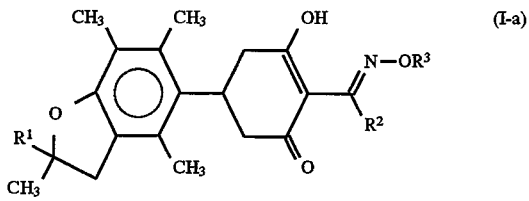

wherein, $R^1$, $R^2$ and $R^3$ are respectively defined as claim 1.

5. The compound according to the claim 1 of formula (I-b)

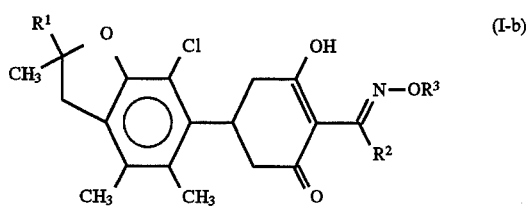

wherein, $R^1$, $R^2$ and $R^3$ are respectively defined as claim 1.

6. The compound according to the claim 1 of formula (I-c)

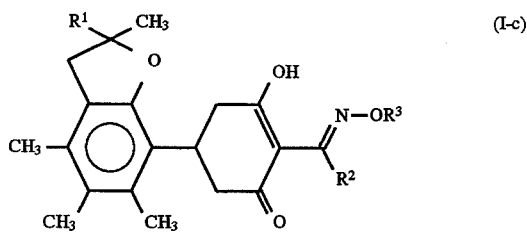

wherein, $R^1$, $R^2$ and $R^3$ are respectively defined as claim 1.

7. The compound according to the claim 1 of formula (I-d)

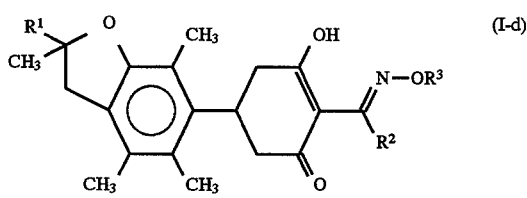

wherein, $R^1$, $R^2$ and $R^3$ are respectively defined as claim 1.

8. The compound according to the claim 1, wherein formula (I) is selected from the group consisting of the following compounds; 5-(2,3-dihydro-2,2,4,6,7-pentamethylbenzofuran-5-yl)-2-[1-(ethoxyimino)propyl]-3-hydroxycyclohex-2-en-1-one, 5-(2,3-dihydro-2,2,4,6,7-pentamethyl-benzofuran-5-yl)-2-[1-(ethoxyimino)butyl]-3-hydroxycyclohex-2-en-1-one, 2-[1-(allyloxyimino) butyl]-5-(2,3-dihydro-2,2,4,6,7-pentamethyl-benzofuran-5-yl)-3-hydroxy-cyclohex-2-en-1-one, 5-(7-chloro-2,3-dihydro-2,2,4,5-tetramethylbenzofuran-6-yl)-2-[1-(ethoxyimino)propyl]-3-hydroxycyclohex-2-en-1-one, 5-(2,3-dihydro-2,2,4,5,6-pentamethylbenzofuran-7-yl)-2-[1-(ethoxyimino) propyl]-3-hydroxy-cyclohex-2-en-1-one, 5-(2,3-dihydro-2,2,4,5,7-pentamethylbenzofuran-6-yl)-2-[1-(ethoxyimino)propyl]-3-hydroxycyclohex-2-en-1 one.

9. A compound of 2-acylcyclohexane-1,3-dione derivatives having formula (IV), as an intermediate of cyclohexane-1,3-dione derivatives of formula (I)

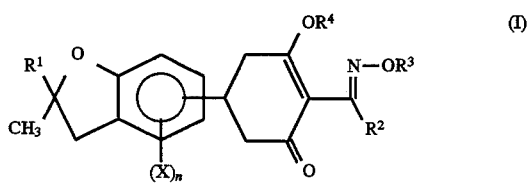

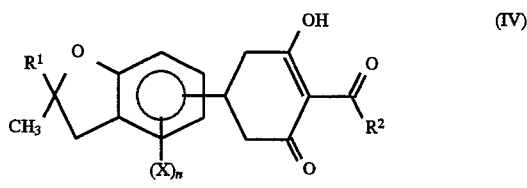

wherein, (X)n, $R^1$, $R^2$, $R^3$ and $R^4$ are respectively defined as claim 1.

10. A process for preparing 2-acyl-1,3-cyclohexandione derivatives having the formula (IV), which consists of preparing the cyclohexenone ester of formula (III) by reacting the 1,3-cyclohexandione derivative of formula (II) with acid chloride or acid anhydride in an inert organic solvent, and being rearranged the above compound (III) in the presence of catalyst,

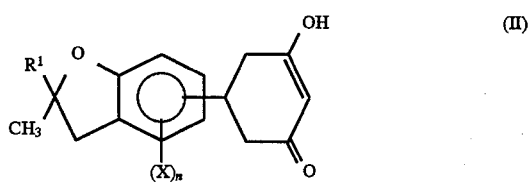

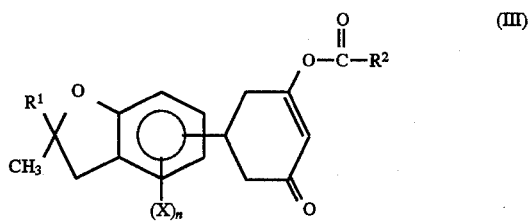

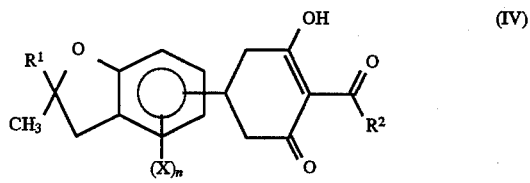

wherein, (X)n, $R^1$ and $R^2$ are respectively defined as claim 1.

11. A cyclohexane-1,3-dione derivative of formula (II), as a starting material of formula (I)

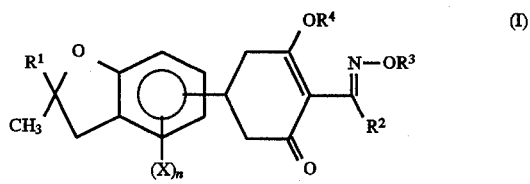

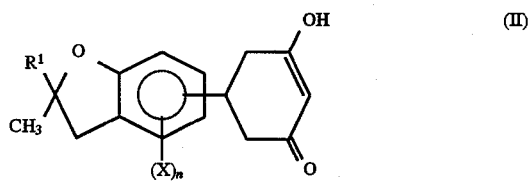

wherein, (X)n, $R^1$, $R^2$ and $R^3$ are respectively defined as claim 1.

12. A process for preparing cyclohexandione derivatives of formula (II), which consist of preparing the cyclohexane-1,3-dione-4-carboxylic acid of formula (VI) by reacting the benzalacetone of the formula (V) with malonic ester in the presence of alkali metal methoxide at refluxing temperature of methanol, and being decarboxylated the compound(VI),

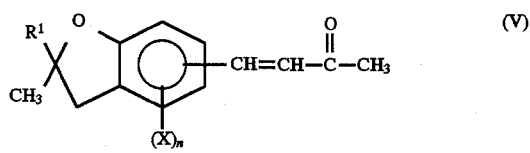

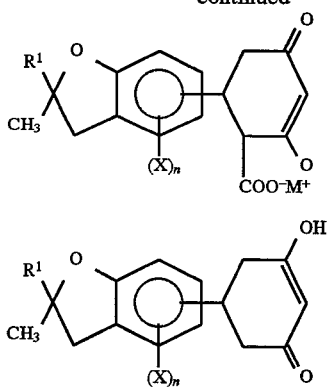

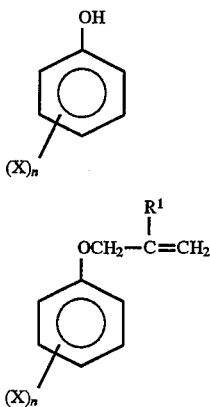

wherein, (X)n and $R^1$ are respectively defined as claim 1.

13. A process for preparing of 2,3-dihydrobenzofuranaldehyde of formula (VII), which consist of preparing the allyl phenyl ether of formula (IX) by reacting the phenol of formula (VIII) with the substituted allyl halide in the presence of base, preparing the 2,3-dihydrobenzofuran of formula (X) by Claisen rearrangement of the compound (IX) and reacting the compound (X) with α, α-dichloromethyl methyl ether in the presence of Lewis acid as catalyst,

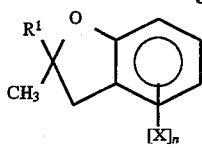

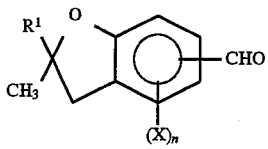

wherein, (X)n, $R^1$ are respectively defined as claim 1.

14. A herbicidal composition comprising as active ingredient a compound as defined according to the claim 1.

15. The herbicide according to the claim 14, wherein the cultivated plant is the broad-leaved plant.

16. The herbicide according to the claim 15, wherein the plant with wide leaf is selected from the group consisting of soybean, cotton, sunflower, sugarbeet and vegetables.

17. The herbicide according to the claim 14, wherein the cultivated plant is selected from the group consisting of rice and wheat.

18. A plant growth regulant containing cyclohexane-1,3-dione derivative of the compound of formula (I) as an active ingredient,

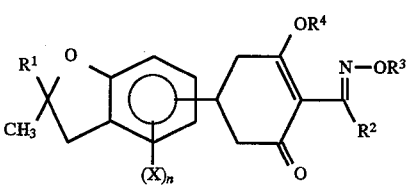

wherein, (X)n, $R^1$, $R^2$, $R^3$ and $R^4$ are respectively defined as claim 1.

* * * * *